(12) United States Patent
Yuan et al.

(10) Patent No.: US 10,551,447 B2
(45) Date of Patent: *Feb. 4, 2020

(54) MAGNETIC FIELD SENSING APPARATUS

(71) Applicant: iSentek Inc., New Taipei (TW)

(72) Inventors: Fu-Te Yuan, New Taipei (TW);
Jen-Tzong Jeng, New Taipei (TW);
Meng-Huang Lai, New Taipei (TW)

(73) Assignee: iSentek Inc., New Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/191,447

(22) Filed: Nov. 15, 2018

(65) Prior Publication Data

US 2019/0101602 A1 Apr. 4, 2019

Related U.S. Application Data

(63) Continuation of application No. 15/287,740, filed on Oct. 7, 2016, now Pat. No. 10,168,398.

(Continued)

(30) Foreign Application Priority Data

Jun. 22, 2016 (TW) .............................. 105119513 A

(51) Int. Cl.
*G01R 33/02* (2006.01)
*G01R 33/09* (2006.01)
(Continued)

(52) U.S. Cl.
CPC ........... *G01R 33/096* (2013.01); *B64G 1/366* (2013.01); *G01N 27/72* (2013.01); *G01N 27/904* (2013.01);
(Continued)

(58) Field of Classification Search
CPC .. B64G 1/366; G01R 33/0206; G01R 33/028; G01R 33/038; G01R 33/1215;
(Continued)

(56) References Cited

U.S. PATENT DOCUMENTS

2005/0140363 A1* 6/2005 Grimm .................. G01R 33/09
324/207.21
2012/0306488 A1* 12/2012 Chen .................... G01R 33/096
324/252

(Continued)

FOREIGN PATENT DOCUMENTS

CN 1717799 1/2006
CN 102809731 12/2012
(Continued)

OTHER PUBLICATIONS

"Office Action of China Counterpart Application," dated Nov. 23, 2018, p. 1-p. 81.

*Primary Examiner* — Raul J Rios Russo
(74) *Attorney, Agent, or Firm* — JCIPRNET

(57) ABSTRACT

A magnetic field sensing apparatus including a magnetic flux concentrator, a plurality of magnetoresistance units, and a plurality of magnetization direction setting elements is provided. The magnetic flux concentrator has a top surface, a bottom surface opposite to the top surface, and a plurality of side surfaces connecting the top surface and the bottom surface. The magnetoresistance units are respectively disposed beside the side surfaces. The magnetoresistance units are electrically connected to form an unchangeable Wheatstone full bridge. The magnetization direction setting elements set the magnetization directions of the magnetoresistance units into three different combinations in three different periods, respectively, so as to enable the unchangeable Wheatstone full bridge to respectively measure the (Continued)

magnetic field components in the three different directions in the three different periods.

20 Claims, 20 Drawing Sheets

Related U.S. Application Data

(60) Provisional application No. 62/242,306, filed on Oct. 16, 2015.

(51) Int. Cl.
| | | |
|---|---|---|
| *G01R 33/12* | (2006.01) | |
| *G01R 15/20* | (2006.01) | |
| *G01R 33/028* | (2006.01) | |
| *G01R 33/038* | (2006.01) | |
| *B64G 1/36* | (2006.01) | |
| *G01N 27/72* | (2006.01) | |
| *G01N 27/90* | (2006.01) | |
| *G01V 3/10* | (2006.01) | |
| *H03K 17/95* | (2006.01) | |
| *G01C 17/02* | (2006.01) | |

(52) U.S. Cl.
CPC ......... *G01R 15/20* (2013.01); *G01R 33/0206* (2013.01); *G01R 33/028* (2013.01); *G01R 33/038* (2013.01); *G01R 33/098* (2013.01); *G01R 33/1215* (2013.01); *G01C 17/02* (2013.01); *G01V 3/101* (2013.01); *G01V 3/107* (2013.01); *H03K 17/9537* (2013.01)

(58) Field of Classification Search
CPC ...... G01R 15/20; G01R 33/098; G01N 27/72; G01N 27/904; G01V 3/101; G01V 3/107; H03K 17/9537
USPC ...... 324/207.21, 207.2, 207.25, 207.13, 251, 324/252, 165, 207.24, 207.1, 11, 207.22, 324/260, 234, 235
See application file for complete search history.

(56) References Cited

U.S. PATENT DOCUMENTS

| | | | |
|---|---|---|---|
| 2015/0137804 A1* | 5/2015 | Yuan | G01R 33/0005 324/244 |
| 2017/0089987 A1* | 3/2017 | Monreal | G01R 33/0023 |
| 2017/0097393 A1* | 4/2017 | Yuan | G01R 33/0005 |

FOREIGN PATENT DOCUMENTS

| | | |
|---|---|---|
| CN | 103033771 | 4/2013 |
| CN | 103261905 | 8/2013 |
| CN | 104656045 | 5/2015 |
| EP | 1046048 | 10/2000 |
| TW | 201430365 | 8/2014 |

* cited by examiner

MAGNETIC FIELD SENSING APPARATUS

CROSS-REFERENCE TO RELATED APPLICATION

This application is a continuation application of U.S. application Ser. No. 15/287,740, filed on Oct. 7, 2016, now allowed, which claims the priority benefits of U.S. provisional application Ser. No. 62/242,306, filed on Oct. 16, 2015, and Taiwan application serial no. 105119513, filed on Jun. 22, 2016. The entirety of each of the above-mentioned patent applications is hereby incorporated by reference herein and made a part of this specification.

BACKGROUND OF THE INVENTION

1. Field of the Invention

The invention generally relates to a magnetic field sensing apparatus.

2. Description of Related Art

With the popularity of portable electronic devices, electronic compass technology capable of sensing a geomagnetic direction has come to attention. When the electronic compass is applied to a portable electronic device with small volume (such as a smart phone), the electronic compass, in addition to being required to comply with the requirement of small volume, is further desired to be capable of achieving a triaxial sensing, and this is because when the smart phone is gripped by a user's hand, it may be slantly gripped, whereby various different grip angles may also be possible. In addition, the electronic compass may also be applied to a drone (e.g., a remote control aircraft, a remote control helicopter, and etc.), and it is also desired that the electronic compass can achieve the triaxial sensing.

A conventional technology achieves the triaxial sensing by means of using complex sensing element, such that, specifically, the triaxial sensing is achieved by using two giant magnetoresistive (GMR) multilayer structures (or tunneling magnetoresistive (TMR) multilayer structures), which are disposed perpendicular to each other, and a hall element. However, since a detection sensitivity of the hall element is different from a detection sensitivity of the GMR multilayer structures (or the TMR multilayer structures), this causes a precision on one of the axes to be different from precisions on the other two axes. As a result, when the user rotates the portable electronic device to a different angle, the detection sensitivities with respect to a same magnetic field are different, thereby causing distress in the use.

In the conventional technology, in order to achieve a multi-axis sensing of the magnetic field, more than two times of manufacturing process are usually used, that is, using manufacturing processes of more than two wafers to manufacture a multi-axial magnetic field sensing module, and thus the overall manufacturing process is complicated and the manufacturing cost is difficult to be lowered. In addition, this also causes the magnetic field sensing apparatus difficult to be further minimized.

SUMMARY OF THE INVENTION

The invention directs to a magnetic field sensing apparatus having a simplified structure and can have a smaller volume.

In one embodiment of the invention, a magnetic field sensing apparatus including a magnetic flux concentrator and a plurality of magnetoresistance units is provided. The magnetic flux concentrator has a top surface, a bottom surface opposite to the top surface, and a plurality of side surfaces connecting the top surface and the bottom surface. The magnetoresistance units are respectively disposed beside the side surfaces. The magnetoresistance units are electrically connected to form at least one kind of Wheatstone full bridge in three different periods so as to respectively measure magnetic field components in three different directions and to enable the at least one kind of Wheatstone full bridge to respectively output three signals corresponding to the magnetic field components in the three different directions.

In the magnetic field sensing apparatus of the embodiment of the invention, the magnetic flux concentrator is used to cause the magnetic field components in the three different directions to bend to directions that can be sensed by the magnetoresistance units, and the magnetic field components in the three different directions, after being bent, have three different combinations of directions passing through the magnetoresistance units. As a result, by electrically connecting the magnetoresistance units to form the at least one kind of Wheatstone full bridge in the three different periods, the magnetic field components in the three different directions can be respectively measured, and the at least one kind of Wheatstone full bridge can respectively output the three signals corresponding to the magnetic field components in the three different directions. Accordingly, the magnetic field sensing apparatus in the embodiment of the invention can have a simplified structure while simultaneously achieving a triaxial magnetic field measurement, and thus can further have a smaller volume.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1A:
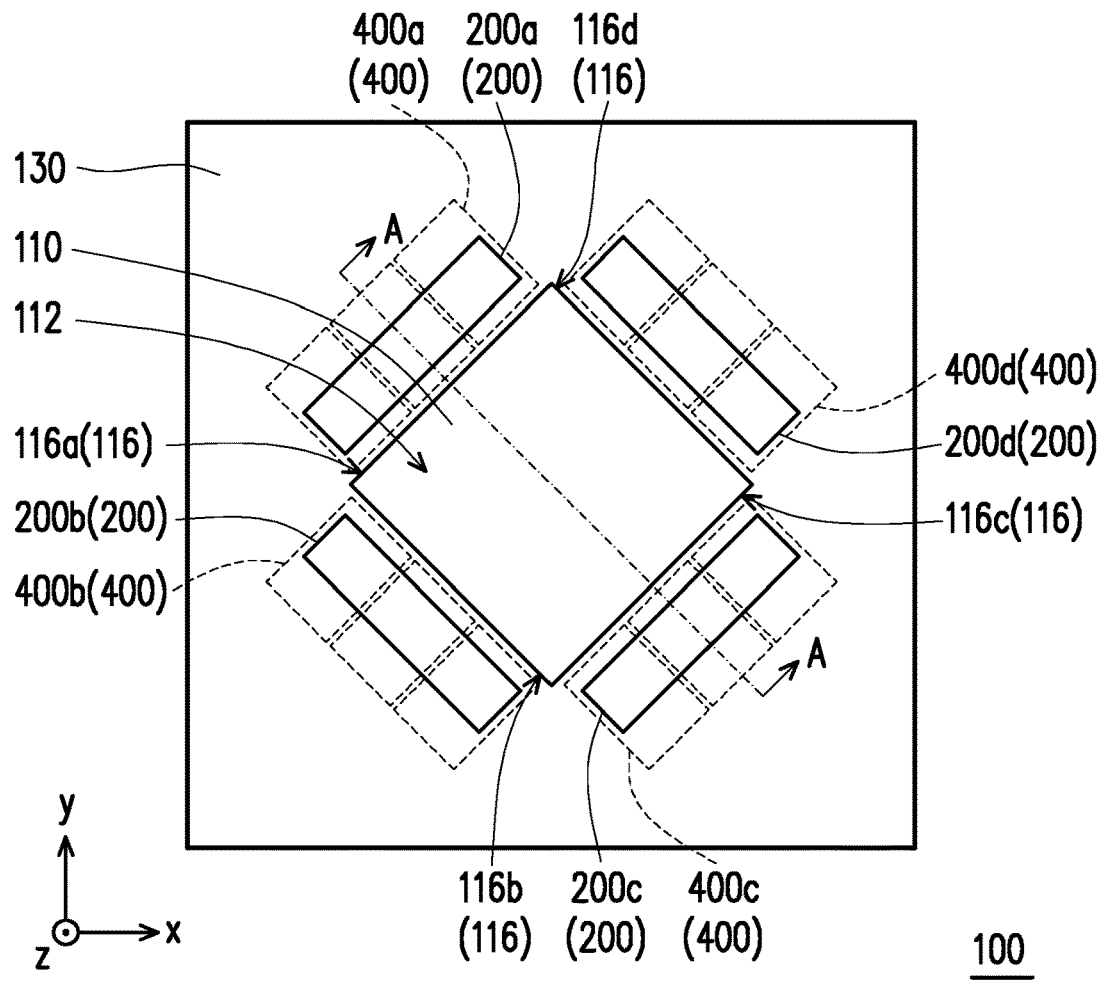
FIG. 1A is a schematic top view illustrating a magnetic field sensing apparatus according to an embodiment of the invention.
Figure 1B:
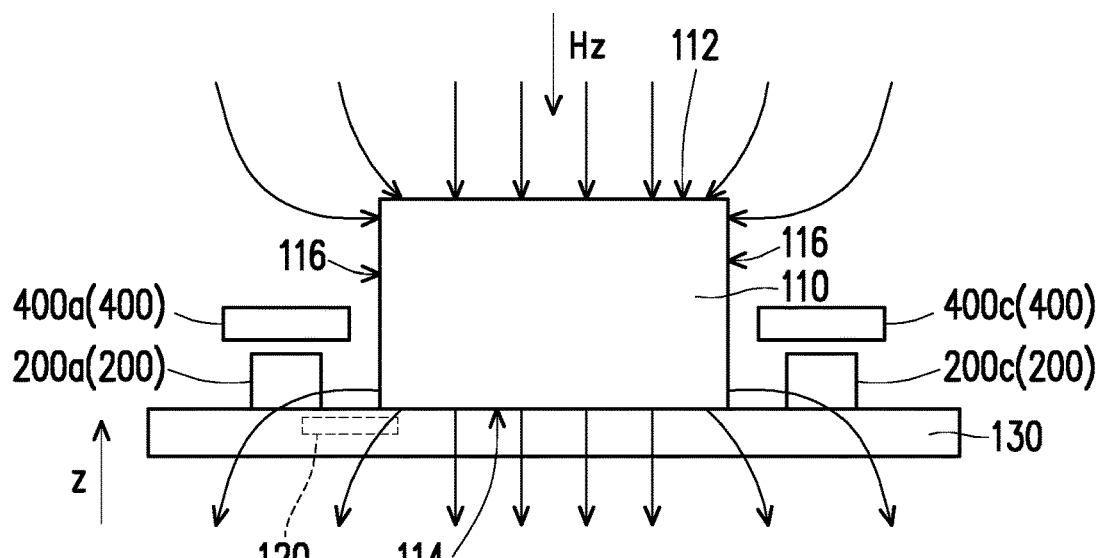
FIG. 1B is a schematic cross-sectional view of the magnetic field sensing apparatus of FIG. 1A along a line A-A.

FIG. 1A is a schematic top view illustrating a magnetic field sensing apparatus according to an embodiment of the invention, and FIG. 1B is a schematic cross-sectional view of the magnetic field sensing apparatus of FIG. 1A along a line A-A. Referring to FIG. 1A and FIG. 1B, the magnetic field sensing apparatus 100 of the present embodiment includes a magnetic flux concentrator 110 and a plurality of magnetoresistance units 200. The magnetic flux concentrator 110 has a top surface 112, a bottom surface 114 opposite to the top surface 112 (as shown in FIG. 1B), and a plurality of side surfaces 116 connecting the top surface 112 and the bottom surface 114, and the magnetoresistance units 200 are respectively disposed beside the side surfaces 116.

In the present embodiment, a material of the magnetic flux concentrator 110 includes a ferromagnetic material with a magnetic permeability greater than 10. In addition, a residual magnetism of the magnetic flux concentrator 110 is, for example, less than 10% of a saturated magnetization thereof. For instance, the magnetic flux concentrator 110 is made of soft magnetic material, such as nickel-iron alloy, ferrocobalt or cobalt-iron-boron alloy, ferrite or other high magnetic permeability material.

Figure 2A:
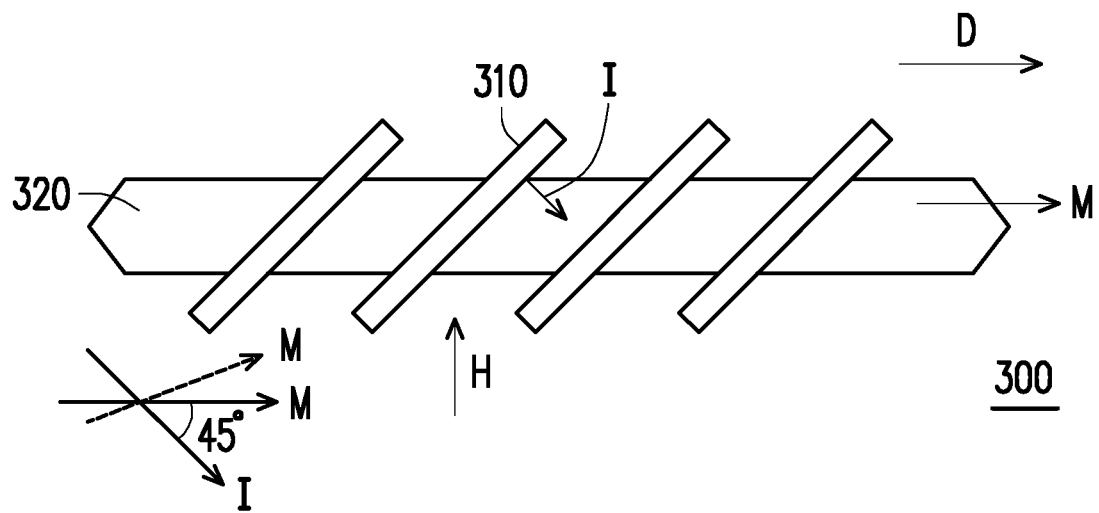
FIG. 2A and FIG. 2B are provided for illustrating the principle of operation of an anisotropic magnetoresistor in FIG. 1A.
Figure 2B:
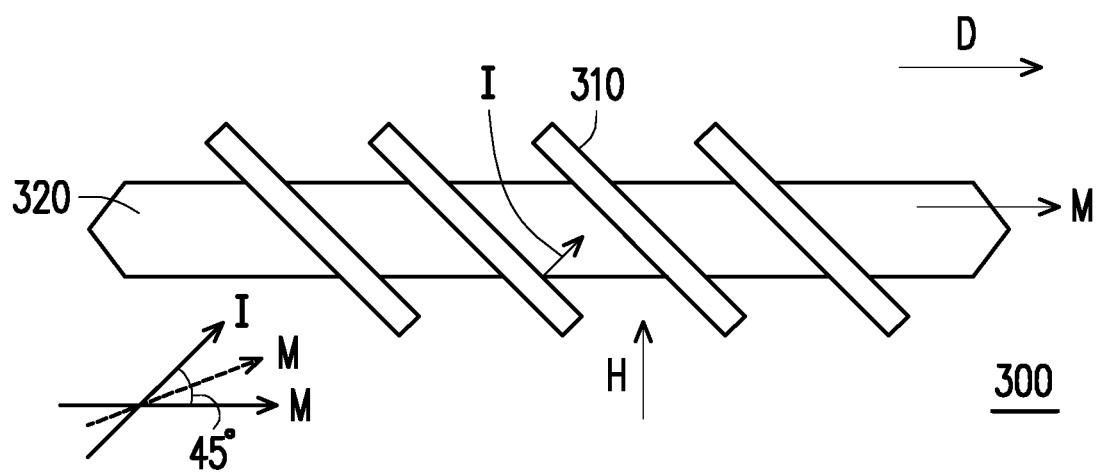

In addition, in the present embodiment, each of the magnetoresistance units 200 includes at least one anisotropic magnetoresistor. FIG. 2A and FIG. 2B are provided for illustrating the principle of operation of an anisotropic magnetoresistor in FIG. 1A. Referring firstly to FIG. 2A, the anisotropic magnetoresistor 300 has a barber pole shaped structure; that is, a surface thereof has a plurality of electrical shorting bars 310 extending and inclining at a 45-degree angle relative to an extending direction D of the anisotropic magnetoresistor, and the electrical shorting bars 310 are spaced apart from each other and disposed in parallel on a ferromagnetic film 320. The ferromagnetic film 320 is a main body of the anisotropic magnetoresistor 300, and an extending direction of the ferromagnetic film 320 is the extending direction of the anisotropic magnetoresistor 300. In addition, two opposite ends of the ferromagnetic film 320 can be made into a tip shape.

The anisotropic magnetoresistor 300, before starting to measure an external magnetic field, can set a magnetization direction thereof through magnetization direction setting elements, wherein the magnetization direction setting elements are, for example, coils, conducting wires, metal sheet or conductors which can generate a magnetic field through being applied an electrical current. In FIG. 2A, the magnetization direction setting elements can generate a magnetic field along the extending direction D through being applied an electrical current, so as to enable the anisotropic magnetoresistor 300 to have a magnetization direction M.

Next, the magnetization direction setting elements are not applied a current, so as to allow the anisotropic magnetoresistor 300 to start measuring the external magnetic field. When there is no external magnetic field, the magnetization direction M of the anisotropic magnetoresistor 300 is kept in the extending direction D, and now, a current I is applied to enable the current I to flow from a left end of the anisotropic magnetoresistor 300 to a right end thereof, wherein a flowing direction of the current I nearby the electrical shorting bars 310 is perpendicular to an extending direction of the electrical shorting bars 310, such that the flowing direction of the current I nearby the electrical shorting bars 310 forms an included angle of 45 degrees with the magnetization direction M, and a resistance of the anisotropic magnetoresistor 300 is R.

When there is an external magnetic field H facing towards a direction perpendicular to the extending direction D, the magnetization direction M of the anisotropic magnetoresistor 300 deflects toward the direction of the external magnetic field H, so that the included angle between the magnetization direction M and the flowing direction of the current I nearby the electrical shorting bars 310 is greater than 45 degrees. At this moment, the resistance of the anisotropic magnetoresistor 300 has a variation of $-\Delta R$, and becomes $R-\Delta R$; that is, the resistance becomes smaller, wherein $\Delta R$ is greater than 0.

However, if as shown in FIG. 2B, when an extending direction of the electrical shorting bars 310 of FIG. 2B is set in a direction forming an included angle of 90 degrees with the extending direction of the electrical shorting bars 310 of FIG. 2A (at this moment, the extending direction of the electrical shorting bars 310 of FIG. 2B still forms an included angle of 45 degrees with the extending direction D of the anisotropic magnetoresistor 300), and when there is an external magnetic field H, then the external magnetic field H still causes the magnetization direction M to deflect towards the direction of the external magnetic field H; at this moment, the included angle between the magnetization direction M and the flowing direction of the current I nearby the electrical shorting bars 310 is smaller than 45 degrees, and thus the resistance of the anisotropic magnetoresistor 300 becomes $R+\Delta R$; that is, the resistance of the anisotropic magnetoresistor 300 becomes larger.

In addition, by using the magnetization direction setting elements to set the magnetization direction M of the anisotropic magnetoresistor in a direction reverse to the one shown in FIG. 2A, the resistance of the anisotropic magnetoresistor 300 of FIG. 2A under the external magnetic field H becomes R+ΔR. Further, by using the magnetization direction setting elements to set the magnetization direction M of the anisotropic magnetoresistor in a direction reverse to the one shown in FIG. 2B, the resistance of the anisotropic magnetoresistor 300 of FIG. 2B under the external magnetic field H becomes R−ΔR.

In view of the above, it can be known that, when the setting direction of the electrical shorting bars 310 is changed, the resistance variation of the anisotropic magnetoresistor 300 changes from +ΔR to −ΔR, or vice versa, in correspondence to the external magnetic field H, and when the magnetization direction M set by the magnetization direction setting elements is reversed, the resistance variation of the anisotropic magnetoresistor 300 changes from +ΔR to −ΔR, or vice versa, in correspondence to the external magnetic field H. When the direction of the external magnetic field H is reversed, the resistance variation of the anisotropic magnetoresistor 300 changes from +ΔR to −ΔR, or vice versa, in correspondence to the external magnetic field H. However, when the flowing direction of the current passing through the anisotropic magnetoresistor 300 is reversed, the resistance variation of the anisotropic magnetoresistor 300 maintains the same positive or negative sign as the original variation in correspondence to the external magnetic field H; that is, if the original variation is +ΔR, then the resulting variation is still +ΔR after the change of current direction, and if the original variation is −ΔR, then the resulting variation is still −ΔR after the change of current direction.

According to the above principles, the variation tendency of the resistance of the anisotropic magnetoresistor 300, namely either the resistance being to become larger or smaller (e.g., either the amount of variation is +ΔR or −ΔR), when the anisotropic magnetoresistor 300 is subjected to a component of the external magnetic field, can be decided through designing the extending direction of the electrical shorting bars 310 or the magnetization direction M set by the magnetization direction setting elements.

Referring to FIG. 1A and FIG. 1B again, in the present embodiment, the extending direction of the anisotropic magnetoresistor in each of the magnetoresistance units 200 is substantially parallel to the corresponding side surface 116, and is substantially parallel to the top surface 112 and the bottom surface 114. Specifically, the extending direction of the anisotropic magnetoresistor in the magnetoresistance unit 200a is substantially parallel to the side surface 116a, the extending direction of the anisotropic magnetoresistor in the magnetoresistance unit 200b is substantially parallel to the side surface 116b, the extending direction of the anisotropic magnetoresistor in the magnetoresistance unit 200c is substantially parallel to the side surface 116c, and the extending direction of the anisotropic magnetoresistor in the magnetoresistance unit 200d is substantially parallel to the side surface 116d.

Figure 3A:
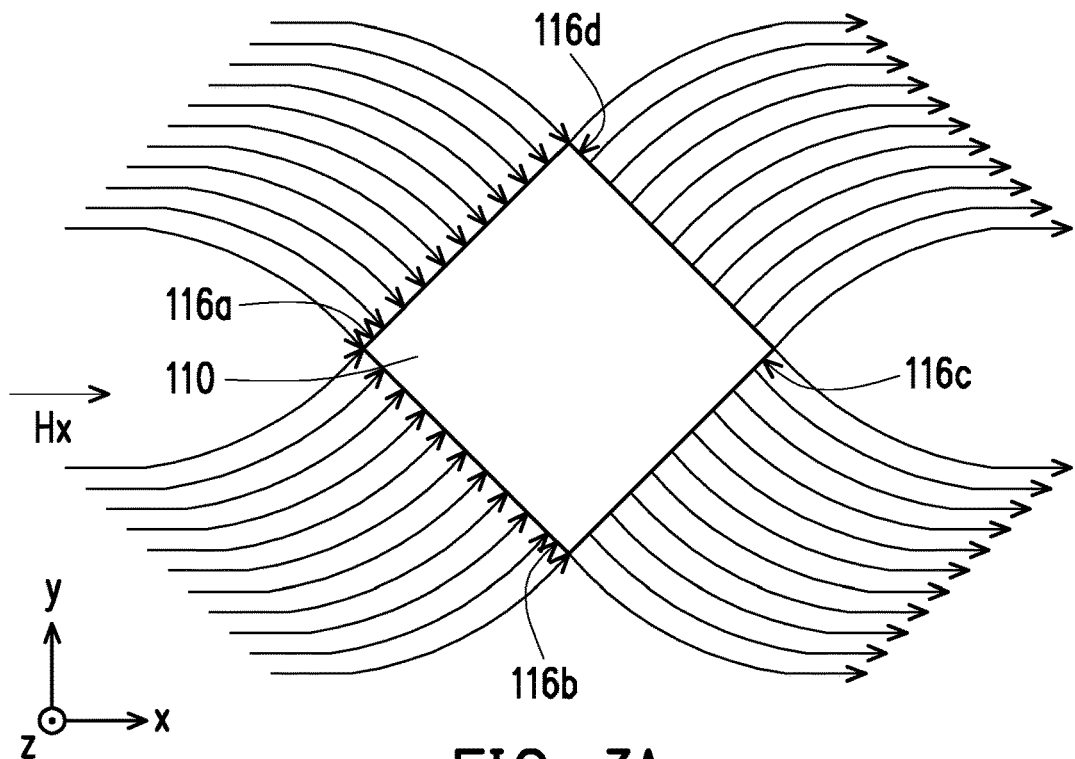
FIG. 3A to FIG. 3C respectively illustrate a deflection state of a plurality of magnetic flux lines when magnetic field components in x-, y- and z-directions pass through a magnetic flux concentrator of FIG. 1A.
Figure 3B:
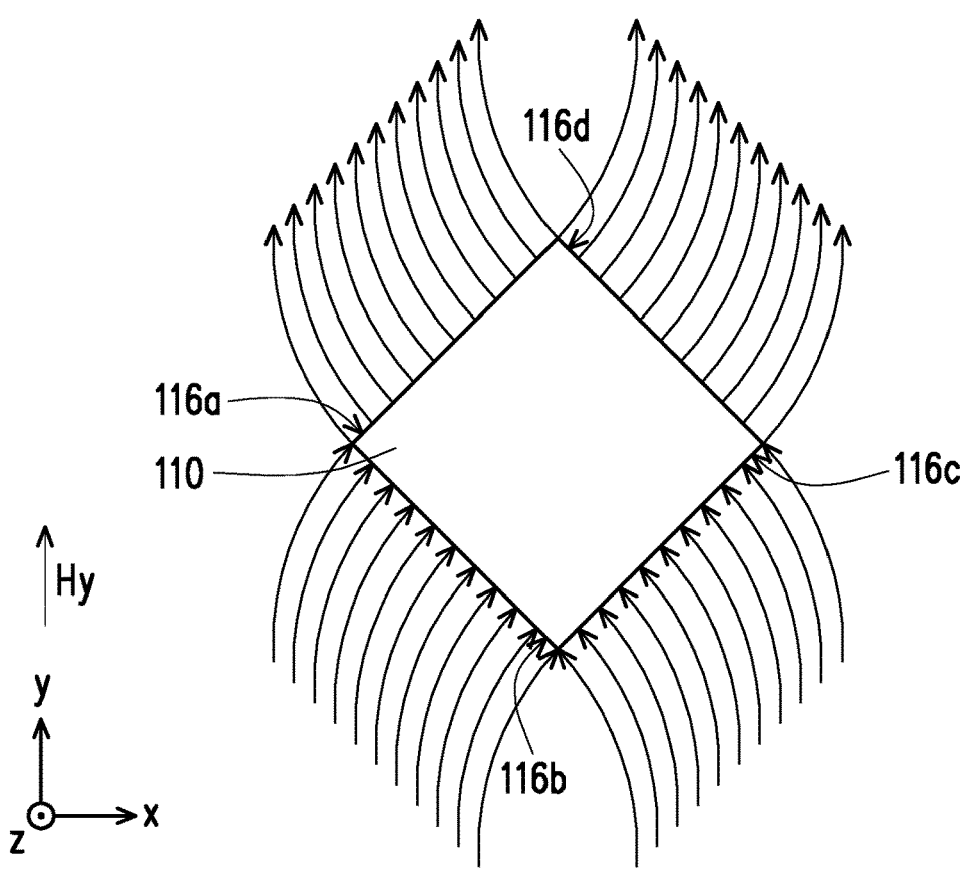
Figure 3C:
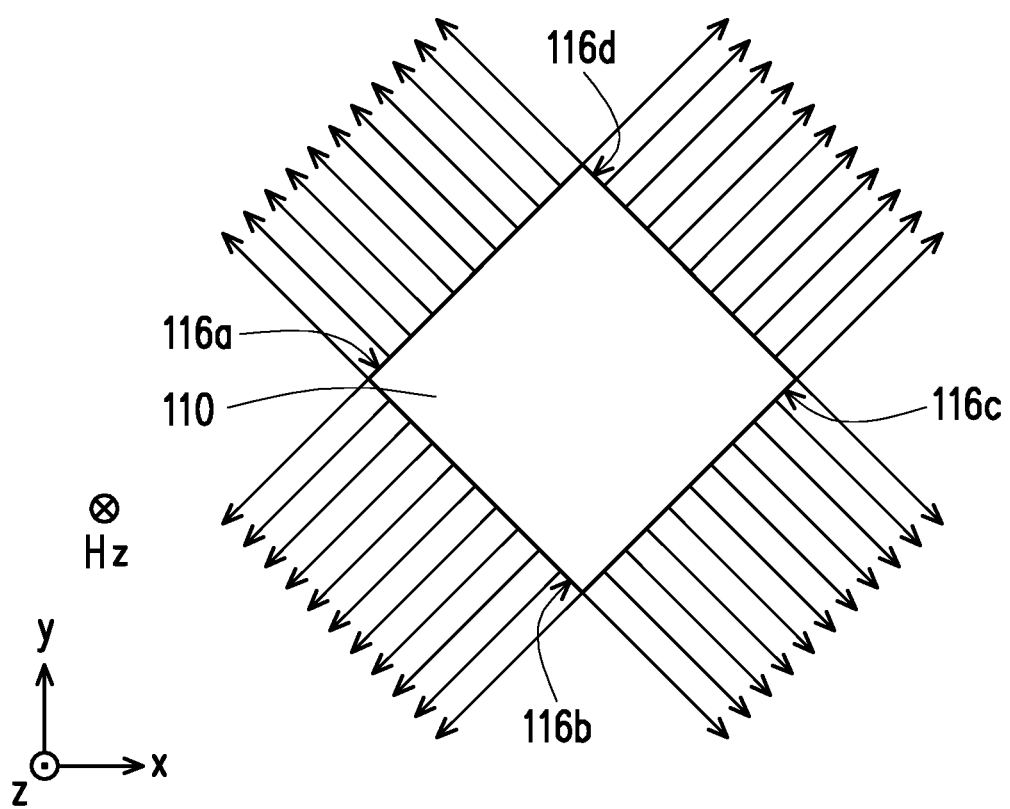

FIG. 3A to FIG. 3C respectively illustrate a deflection state of a plurality of magnetic flux lines when magnetic field components in x-, y- and z-directions pass through the magnetic flux concentrator 110 of FIG. 1A. Referring to FIG. 1A, FIG. 1B and FIG. 3A, a space in which the magnetic field sensing apparatus 100 of the present embodiment locates can be defined by using a Cartesian coordinate system, wherein the x-direction and the y-direction are substantially parallel to the two diagonal lines of the top surface 112, respectively, and the z-direction is substantially perpendicular to the top surface 112. In addition, the x-direction, the y-direction and the z-direction are perpendicular to each other. In the present embodiment, the top surface 112, for example, appears to be a square, wherein 4 side surfaces 116 thereof are all substantially perpendicular to the top surface 112, and any two adjacent side surfaces 116 are substantially perpendicular to each other, that is, normal lines of any two adjacent side surfaces 116 are substantially perpendicular to each other. In other words, the x-direction and the y-direction fall on a plane parallel to a plurality of normal lines of the four side surfaces 116, and substantially form an included angle of 45 degrees with the normal lines.

Figure 4A:
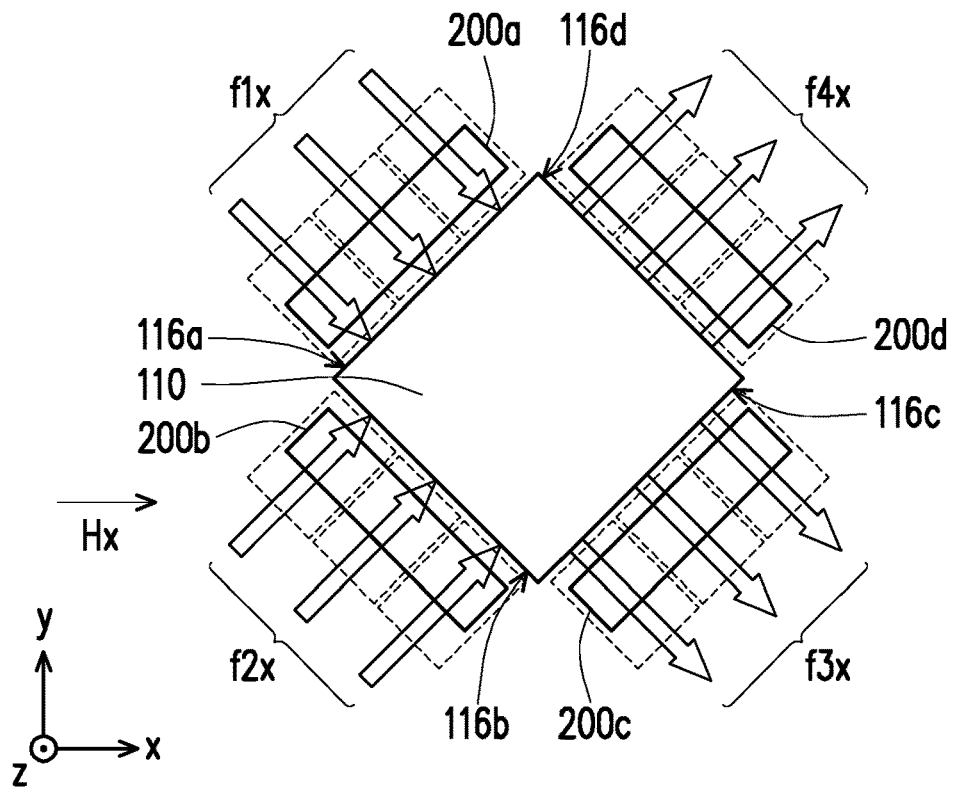
FIG. 4A to FIG. 4C respectively illustrate the magnetic field components nearby the sides of the magnetic flux concentrator of FIG. 1A when the magnetic field components in the x-, y- and z-directions pass through the magnetic flux concentrator.

As shown in FIG. 3A, when a magnetic field component Hx along the +x-direction passes through the magnetic flux concentrator 110, a direction of magnetic flux lines of the magnetic field component Hx when passing through a vicinity of the magnetic flux concentrator 110 is intended to change to be perpendicular to directions of the surfaces of the magnetic flux concentrator 110 (e.g., the side surfaces 116a, 116b, 116c and 116d). As a result, when there is a magnetic field component Hx of an external magnetic field along the +x-direction, as shown in FIG. 4A, magnetic field components f1x, f2x, f3x and f4x are respectively generated at the magnetoresistance units 200a, 200b, 200c and 200d beside the side surfaces 116a, 116b, 116c and 116d.

Figure 4B:
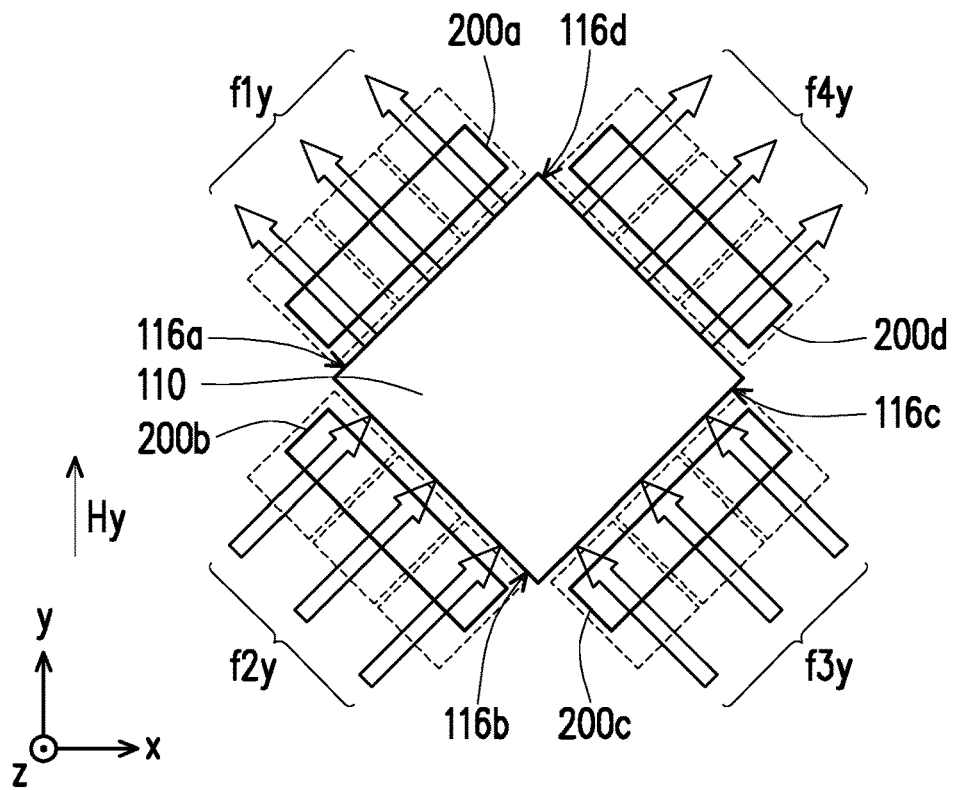

Referring further to FIG. 3B and FIG. 4B, when a magnetic field component Hy along the +y-direction passes through the magnetic flux concentrator 110, a direction of magnetic flux lines of the magnetic field component Hy when passing through the vicinity of the magnetic flux concentrator 110 is intended to change to be perpendicular to the directions of the surfaces 116a, 116b, 116c and 116d of the magnetic flux concentrator 110. As a result, when there is a magnetic field component Hy of an external magnetic field along the +y-direction, as shown in FIG. 4B, magnetic field components f1y, f2y, f3y and f4y are respectively generated at the magnetoresistance units 200a, 200b, 200c and 200d beside the side surfaces 116a, 116b, 116c and 116d.

Figure 4C:
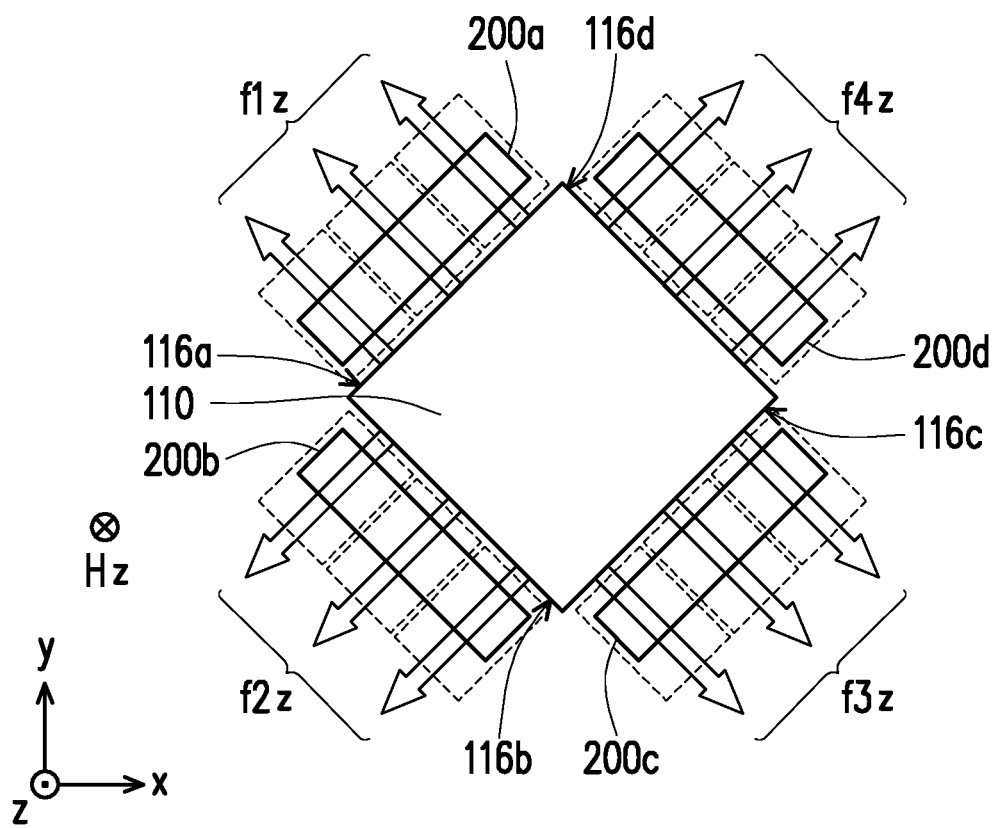

Referring further to FIG. 1B and FIG. 4C, when a magnetic field component Hz along the −z-direction passes through the magnetic flux concentrator 110, a direction of magnetic flux lines of the magnetic field component Hz when passing through a vicinity of the side surfaces 116 of the magnetic flux concentrator 110 is intended to change to be perpendicular to the directions of the surfaces 116a, 116b, 116c and 116d of the magnetic flux concentrator 110. As a result, when there is a magnetic field component Hz of an external magnetic field along the −z-direction, as shown in FIG. 4C, magnetic field components f1z, f2z, f3z and f4z are respectively generated at the magnetoresistance units 200a, 200b, 200c and 200d beside the side surfaces 116a, 116b, 116c and 116d.

Figure 5A:
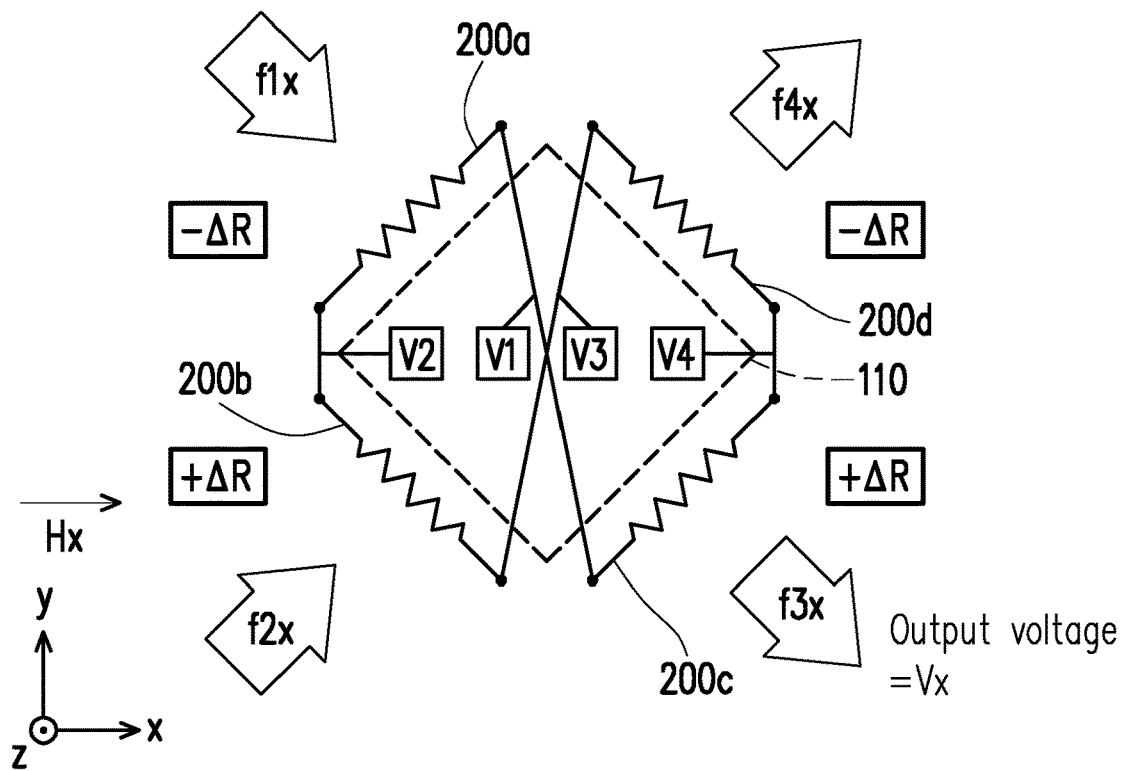
FIG. 5A, FIG. 5B and FIG. 5C are equivalent circuit diagrams of a magnetic field sensing apparatus in a first embodiment of the invention when measuring the magnetic field component in the x-direction.
Figure 5B:
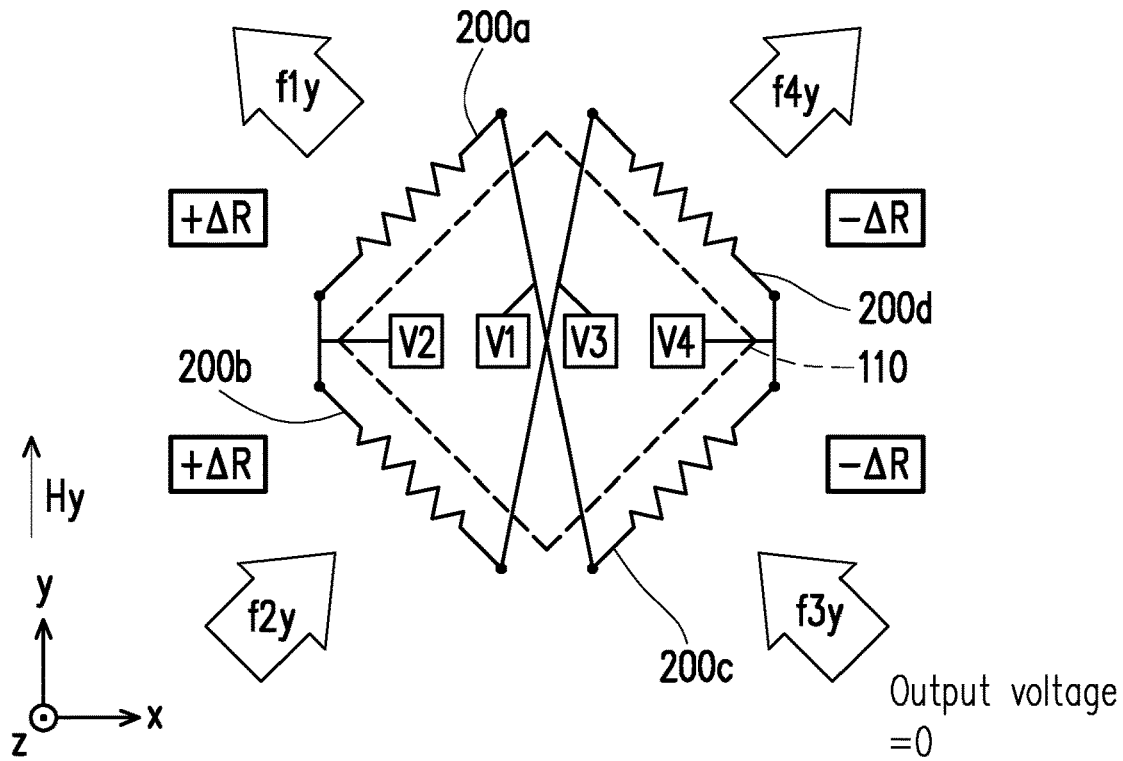
Figure 5C:
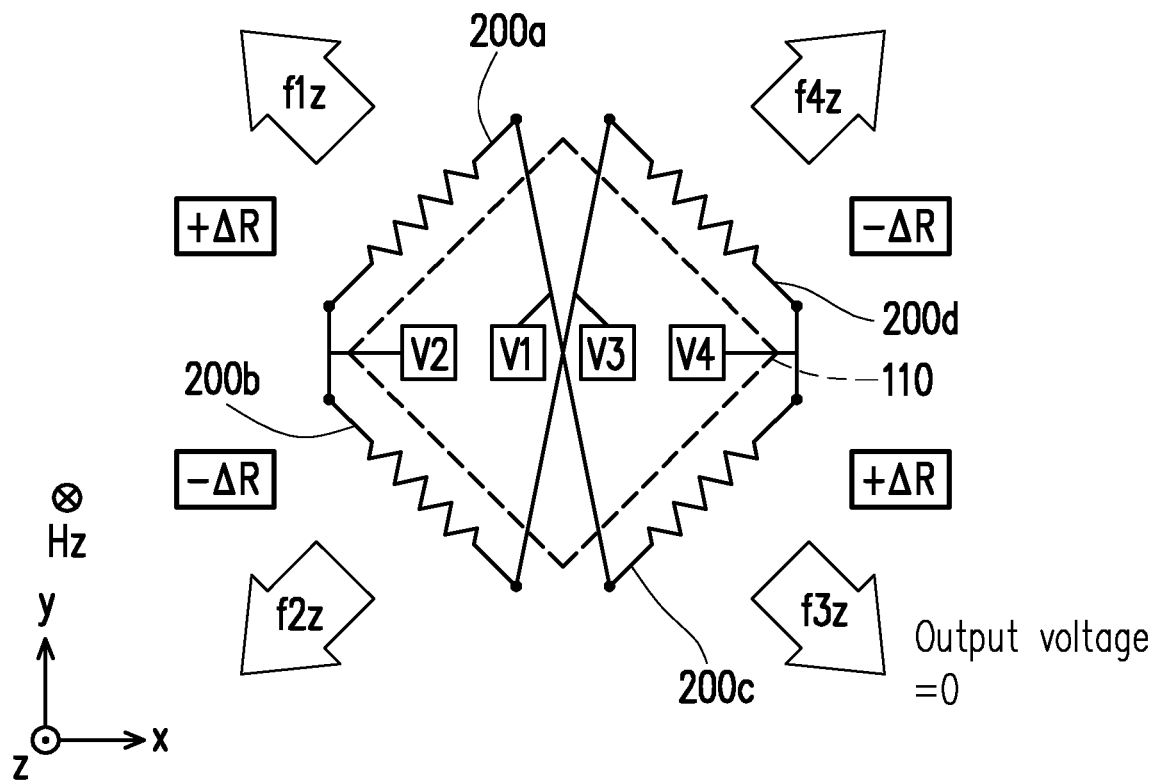
Figure 6A:
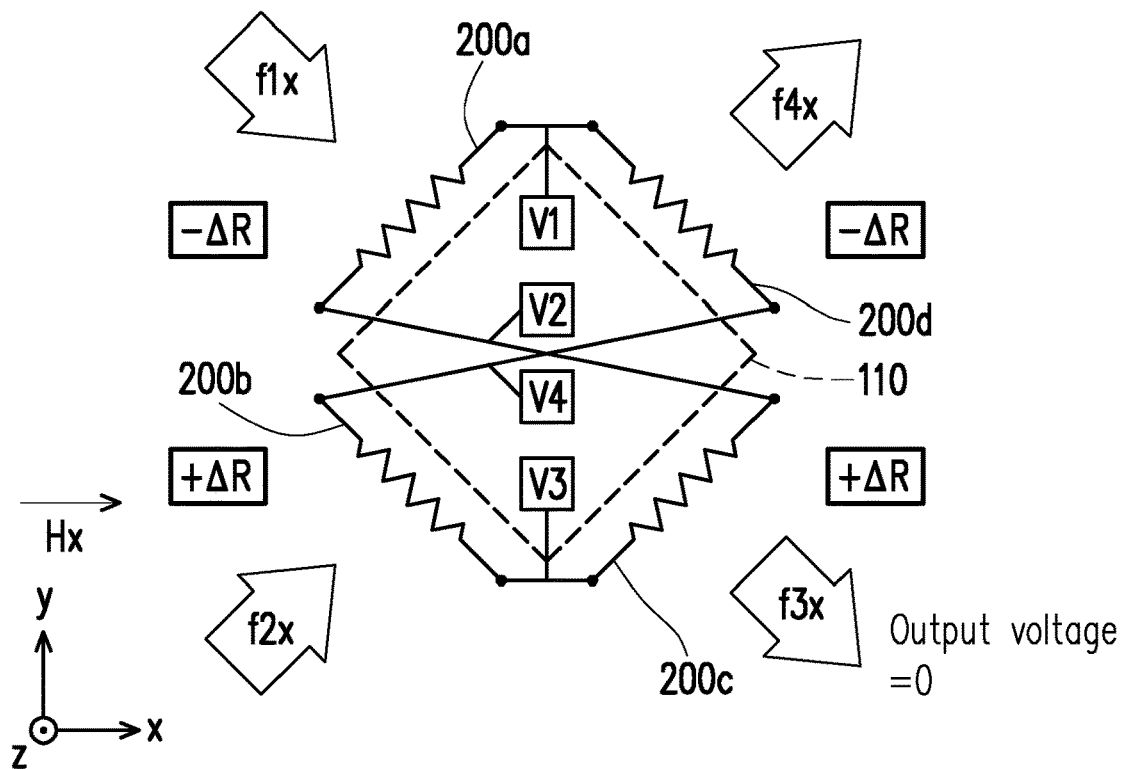
FIG. 6A, FIG. 6B and FIG. 6C are equivalent circuit diagrams of the magnetic field sensing apparatus in the first embodiment of the invention when measuring the magnetic field component in the y-direction.
Figure 6B:
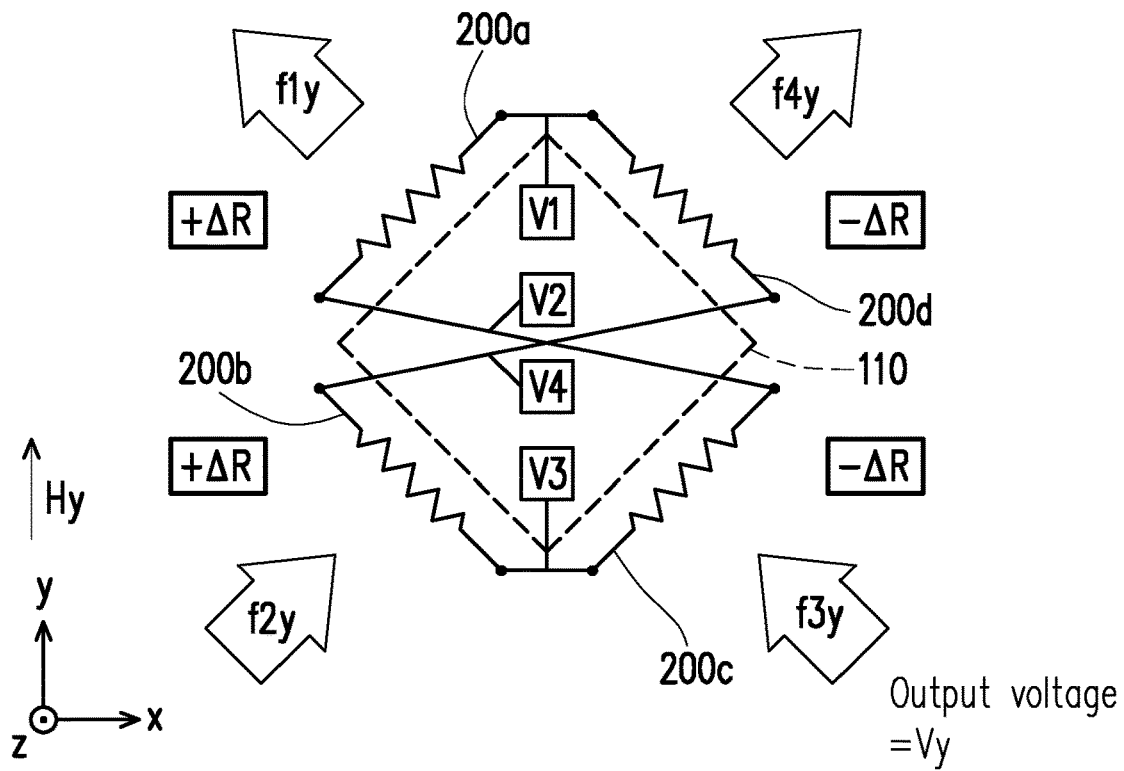
Figure 6C:
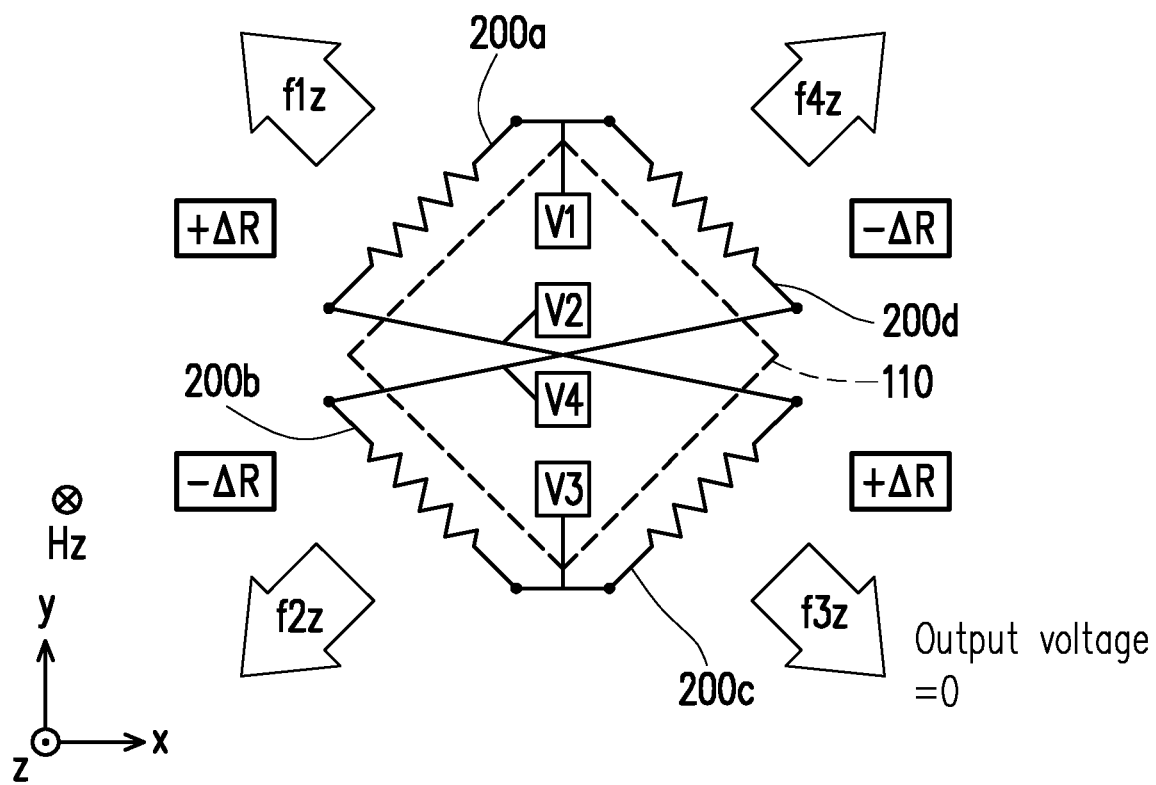
Figure 7A:
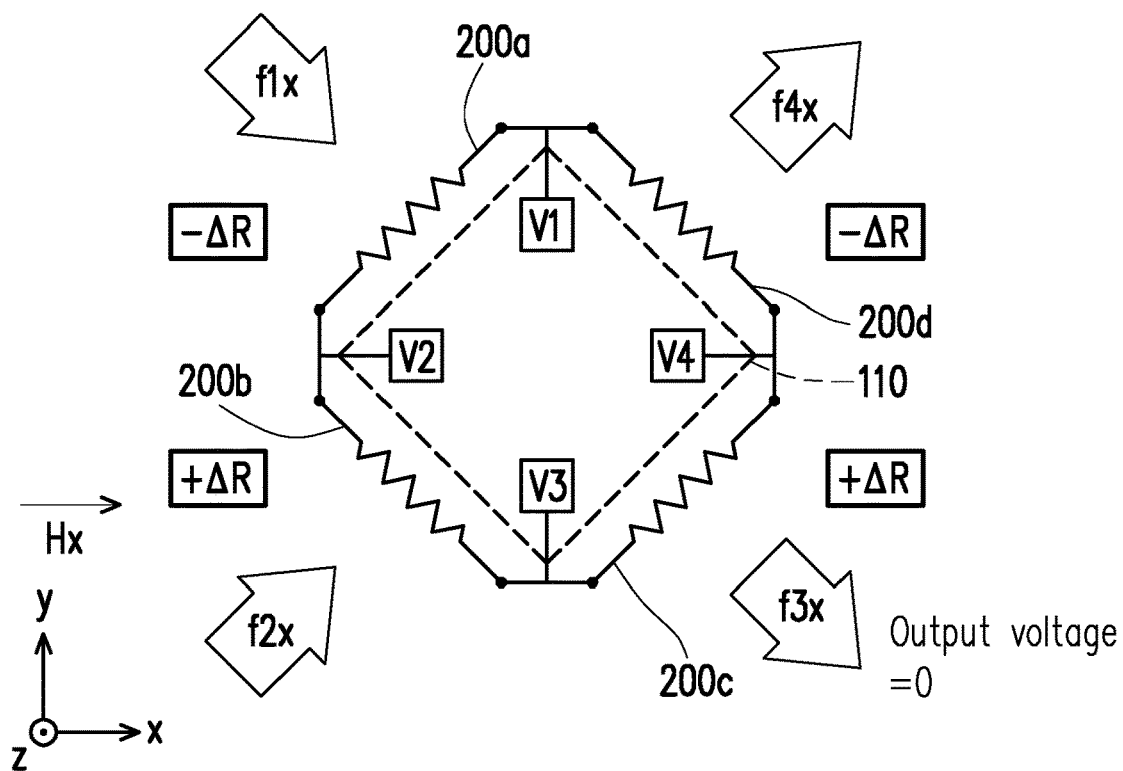
FIG. 7A, FIG. 7B and FIG. 7C are equivalent circuit diagrams of the magnetic field sensing apparatus in the first embodiment of the invention when measuring the magnetic field component in the z-direction.
Figure 7B:
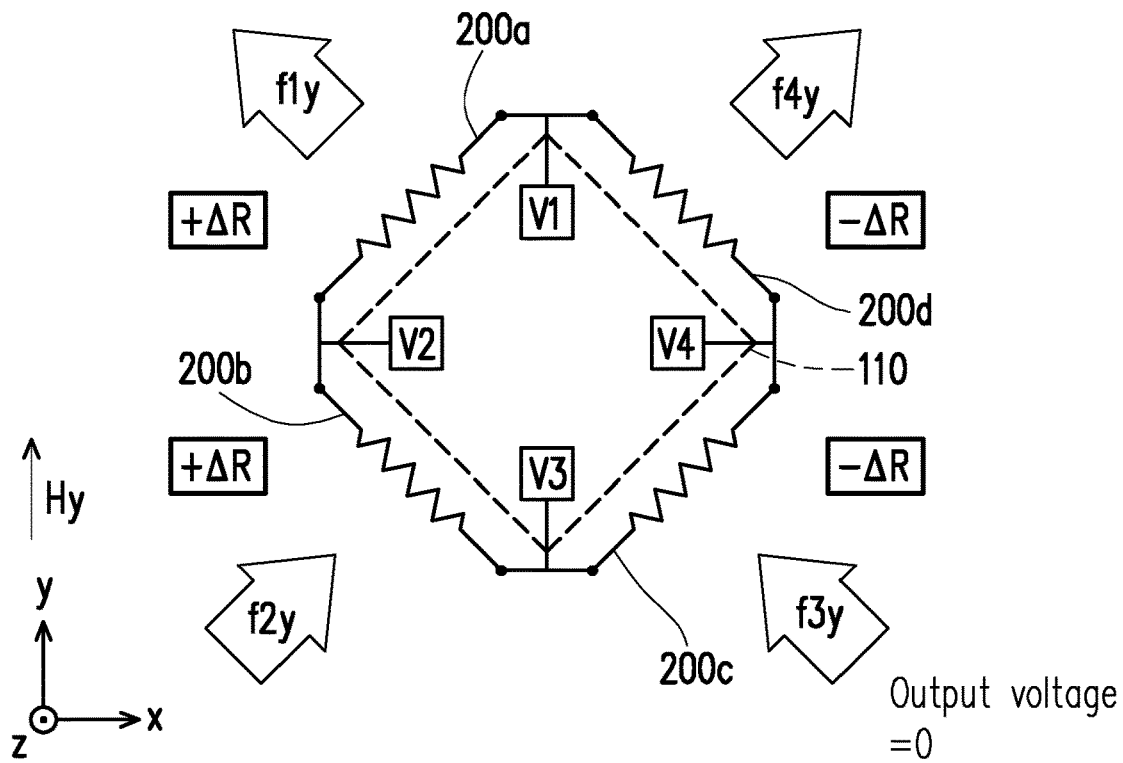
Figure 7C:
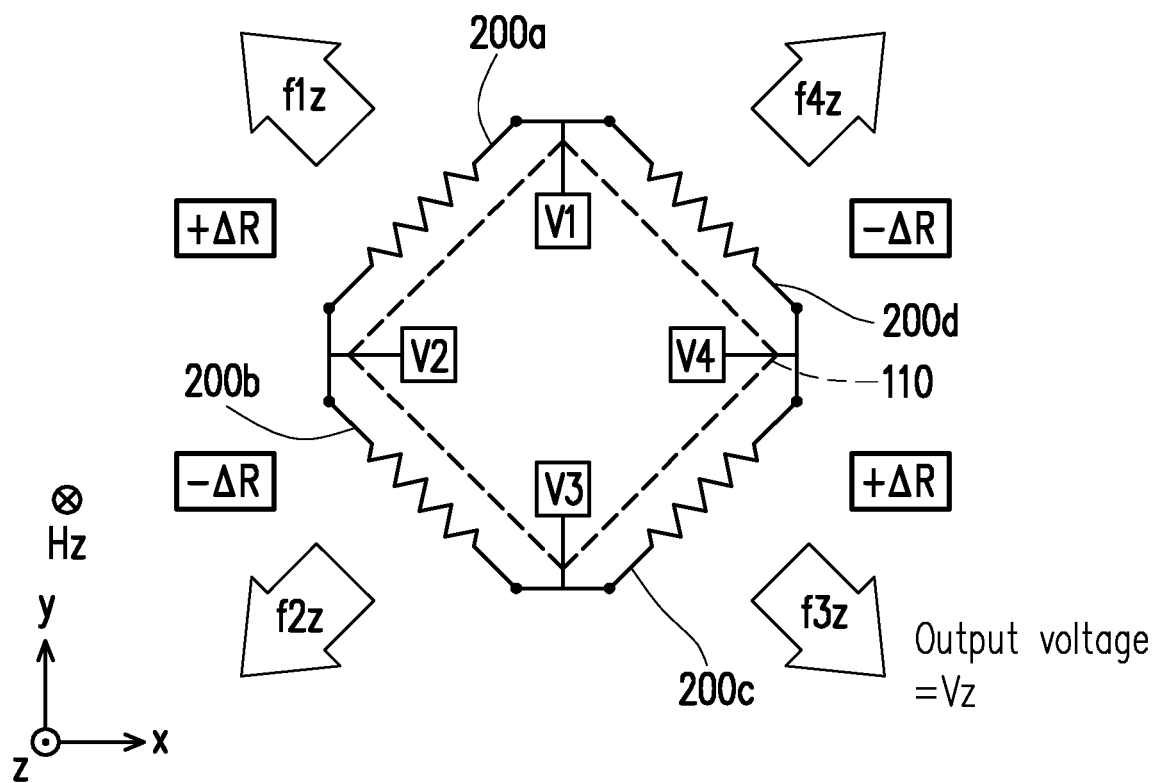

FIG. 5A, FIG. 5B and FIG. 5C are equivalent circuit diagrams of a magnetic field sensing apparatus in a first embodiment of the invention when measuring the magnetic field component in the x-direction, FIG. 6A, FIG. 6B and FIG. 6C are equivalent circuit diagrams of the magnetic field sensing apparatus in the first embodiment of the invention when measuring the magnetic field component in the y-direction, and FIG. 7A, FIG. 7B and FIG. 7C are equivalent circuit diagrams of the magnetic field sensing apparatus in the first embodiment of the invention when measuring the magnetic field component in the z-direction. Referring to FIG. 1A, FIG. 5A to FIG. 5C, FIG. 6A to FIG. 6C and FIG. 7A to FIG. 7C, element configurations of the magnetic field sensing apparatus 100 of the first embodiment are as shown in FIG. 1A and FIG. 1B, wherein the equivalent circuit diagrams thereof when measuring the magnetic field component 1-Ix in the x-direction are as shown in FIG. 5A to FIG. 5C, the equivalent circuit diagrams thereof when measuring the magnetic field component Hy in the y-direction are as shown in FIG. 6A to FIG. 6C, and the equivalent circuit diagrams thereof when measuring the magnetic field component Hz in the z-direction are as shown in FIG. 7A to FIG. 7C.

In the present embodiment, the magnetoresistance units 200 (including the magnetoresistance units 200a, 200b, 200c and 200d) are electrically connected to form at least one kind of Wheatstone full bridge (in the present embodiment, for instance, there are three kinds of Wheatstone full bridges such as the first kind of Wheatstone full bridge in FIG. 5A to FIG. 5C, the second kind of Wheatstone full bridge in FIG. 6A to FIG. 6C and the third kind of Wheatstone full bridge in FIG. 7A to FIG. 7C) in three different periods, so as to respectively measure the magnetic field components (e.g., the magnetic field components Hx, Hy and Hz) in the three different directions (namely, the first direction (e.g., the x-direction), the second direction (e.g., the y-direction) and the third direction (e.g., the z-direction)), thereby enabling the at least one kind of Wheatstone full bridge (e.g., the aforementioned three kinds of Wheatstone full bridges) output three signals respectively corresponding to the magnetic field components (e.g., the magnetic field components Hx, Hy and Hz) in the three different directions (e.g., the x-direction, the y-direction and the z-direction). In other embodiments, the three different directions do not necessarily have to be perpendicular to each other, and may also have at least two directions not being perpendicular to each other.

In the present embodiment, the bottom surface 114 is substantially parallel to the top surface 112, and is, for example, also a square. The two diagonal lines of the bottom surface 114 are respectively parallel to two of the three different directions (e.g., the x-direction and the y-direction), and the remaining one of three different directions (e.g., the z-direction) is substantially perpendicular to the bottom surface 114.

In the present embodiment, the magnetic field sensing apparatus 100 further includes a switching circuit 120 electrically connected to the magnetoresistance units 200a, 200b, 200c and 200d, and the switching circuit 120 electrically connects the magnetoresistance units 200a, 200b, 200c and 200d to form three kinds of Wheatstone full bridges, such as the first kind of Wheatstone full bridge shown in FIG. 5A to FIG. 5C, the second kind of Wheatstone full bridge shown in FIG. 6A to FIG. 6C and the third kind of Wheatstone full bridge shown in FIG. 7A to FIG. 7C, in three different periods, respectively. The three kinds of Wheatstone full bridges respectively measure the magnetic field components (e.g., the magnetic field components Hx, Hy and Hz) in the three different directions (e.g., the x-direction, the y-direction and the z-direction) and respectively output the three signals corresponding to the magnetic field components (e.g., the magnetic field components Hx, Hy and Hz) in the three different directions.

In the present embodiment, the magnetic field sensing apparatus 100 further includes a substrate 130, wherein the magnetic flux concentrator 110 and the magnetoresistance units 200 are disposed on the substrate 130, and the switching circuit 120 is disposed in the substrate 130. The substrate 130 is, for example, a semiconductor substrate (e.g., a silicon substrate), a glass substrate or a circuit substrate, wherein the circuit substrate is, for example, configured with conductive traces, and is a silicon substrate covered with an insulation layer on a surface thereof.

In the present embodiment, in any one of the three different periods, the signal outputted by the at least one kind of Wheatstone full bridge is a differential signal corresponding to the magnetic field component in one of the three different directions, and at this moment, differential signals generated by the at least one kind of Wheatstone full bridge and corresponding to the magnetic field components in the remaining two of the three different directions are both zero. For instance, in the first period of the three different periods, as shown n FIG. 5A to FIG. 5C, the signal outputted by the first kind of Wheatstone full bridge is a differential signal corresponding to the magnetic field component Hx in one direction (e.g., the x-direction) of the three different directions (namely, the x-, y- and z-directions), and at this moment, differential signals generated by the first kind of Wheatstone full bridge and corresponding to the magnetic field components Hy and Hz in the remaining two directions (namely, the y- and z-directions) of the three different directions are both 0. In addition, in the second period of the three different periods, as shown in FIG. 6A to FIG. 6C, the signal outputted by the second kind of Wheatstone full bridge is a differential signal corresponding to the magnetic field component Hy in one direction (e.g., the y-direction) of the three different directions (namely, the x-, y- and z-directions), and at this moment, differential signals generated by the second kind of Wheatstone full bridge and corresponding to the magnetic field components Hx and Hz in the remaining two directions (namely, the x- and z-directions) of the three different directions are both 0. Furthermore, in the third period of the three different periods, as shown in FIG. 7A to FIG. 7C, the signal outputted by the third kind of Wheatstone full bridge is a differential signal corresponding to the magnetic field component Hz in one direction (e.g., the z-direction) of the three different directions (namely, the x-, y- and z-directions), and at this moment, differential signals generated by the third kind of Wheatstone full bridge and corresponding to the magnetic field components Hx and Hy in the remaining two directions (namely, the x- and y-directions) of the three different directions are both 0.

In addition, in the present embodiment, in any one of the three different periods, the number of the Wheatstone full bridge formed by electrically connecting the magnetoresistance units 200 is one.

Specifically, in the first period of the three different periods, referring firstly to FIG. 5A, the magnetic field components f1x, f2x, f3x and f4x are respectively generated at the magnetoresistance units 200a, 200b, 200c and 200d when the external magnetic field has the magnetic field component Hx. In the present embodiment, the magnetic field sensing apparatus 100 (please refer to FIG. 1A) further includes a plurality of magnetization direction setting elements 400 respectively disposed beside the magnetoresistance units 200. For instance, the magnetization direction setting elements 400a, 400b, 400c and 400d are respectively disposed beside the magnetoresistance units 200a, 200b, 200c and 200d. The magnetization direction setting elements 400 can be disposed above, below or both above and below the magnetoresistance units 200, so as to set the magnetization directions of the magnetoresistance units 200. With the configurations as described in the associated paragraphs of FIG. 2A and FIG. 2B (including the setting direction of the electrical shorting bars 310 and the setting directions of the initial magnetization directions of the magnetoresistance units 200), the magnetoresistance units 200a, 200b, 200c and 200d can respectively generate the resistance variations of −ΔR, +ΔR, −ΔR and +ΔR in correspondence to the magnetic field components f1x, f2x, f3x and f4x. As a result, when a voltage difference is applied between a contact V2 and a contact V4, there is a voltage difference, such as an output voltage Vx, existing between a contact V1 and contact V3, and the output voltage Vx is, namely, a differential signal, in which a size thereof is corresponded to the size of the magnetic field component Hx. Therefore, by knowing the size of the output voltage Vx, it is able to deduce the size of the magnetic field component Hx.

On the other hand, referring to FIG. 5B, the magnetic field components f1y, f2y, f3y and f4y are respectively generated at the magnetoresistance units 200a, 200b, 200c and 200d when the external magnetic field has the magnetic field component Hy. Since the direction of the magnetic field component f1y is reverse to that of the magnetic field component f1x of FIG. 5A, the resistance variation of the magnetoresistance unit 200a is changed to +ΔR. In addition, since the direction of the magnetic field component f3y is reverse to that of the magnetic field component f3x of FIG. 5A, the resistance variation of the magnetoresistance unit 200c is changed to −ΔR. As a result, the magnetoresistance units 200a, 200b, 200c and 200d respectively generate the resistance variations of +ΔR, +ΔR, −ΔR and −ΔR in correspondence to the magnetic field components f1y, f2y, f3y and f4y. Therefore, when a voltage difference is applied between the contact V2 and the contact V4, a voltage difference between the contact V1 and the contact V3 is substantially 0, that is, the differential signal as currently outputted is zero.

Furthermore, referring to FIG. 5C, when the external magnetic field has the magnetic field component Hz, the magnetic field components f1z, f2z, f3z and f4z are respectively generated at the magnetoresistance units 200a, 200b, 200c and 200d. At this moment, the magnetoresistance units 200a, 200b, 200c and 200d respectively generate the resistance variations of +ΔR, −ΔR, +ΔR and −ΔR in correspondence to the magnetic field components f1z, f2z, f3z and f4z. Therefore, when a voltage difference is applied between the contact V2 and the contact V4, a voltage difference between the contact V1 and the contact V3 is substantially 0, that is, the differential signal as currently outputted is zero.

Accordingly, when the magnetoresistance units 200a, 200b, 200c and 200d are electrically connected to form the first kind of Wheatstone full bridge as shown in FIG. 5A to FIG. 5C, the magnetic field components Hy and Hz do not contribute to the voltage outputted by the contact V1 and V3. At this moment, the output voltage Vx is only related to the magnetic field component Hx, and thus the first kind of Wheatstone full bridge can be used to measure the magnetic field component Hx in the x-direction. In the first kind of Wheatstone full bridge: the magnetoresistance unit 200a and the magnetoresistance unit 200c are connected in series, the magnetoresistance unit 200b and the magnetoresistance unit 200d are connected in series, then the aforementioned two serial connections are further connected in parallel, the contact V2 is electrically connected between the magnetoresistance unit 200a and the magnetoresistance unit 200b, the contact V4 is electrically connected between the magnetoresistance unit 200c and the magnetoresistance unit 200d, the contact V1 is electrically connected between the magnetoresistance unit 200a and the magnetoresistance unit 200c, and the contact V3 is electrically connected between the magnetoresistance unit 200b and the magnetoresistance unit 200d.

In the second period of the three different periods, referring to FIG. 6A again, the switching circuit 120 electrically connects the magnetoresistance units 200a, 200b, 200c and 200d to form the second kind of Wheatstone full bridge. In the second kind of Wheatstone full bridge: the magnetoresistance unit 200a and the magnetoresistance unit 200c are connected in series, the magnetoresistance unit 200d and the magnetoresistance unit 200b are connected in series, then the aforementioned two serial connections are further connected in parallel, the contact V1 is electrically connected between the magnetoresistance unit 200a and the magnetoresistance unit 200d, the contact V3 is electrically connected between the magnetoresistance unit 200b and the magnetoresistance unit 200c, the contact V2 is electrically connected between the magnetoresistance unit 200a and the magnetoresistance unit 200c, and the contact V4 is electrically connected between the magnetoresistance unit 200d and the magnetoresistance unit 200b. The setting directions of the initial magnetization directions of the magnetoresistance units 200a, 200b, 200c and 200d are identical to that of FIG. 5A to FIG. 5C, and thus when the external magnetic field has the magnetic field component Hx, the magnetoresistance units 200a, 200b, 200c and 200d also respectively generate the resistance variations of −ΔR, +ΔR, −ΔR and +ΔR in correspondence to the magnetic field components f1x, f2x, f3x and f4x. As a result, when a voltage difference is applied between the contact V1 and the contact V3, a voltage difference between the contact V2 and the contact V4 is substantially 0, that is, a differential signal as being outputted is 0.

On the other hand, referring to FIG. 6B, when the external magnetic field has the magnetic field component Hy, the magnetoresistance units 200a, 200b, 200c and 200d respectively generate the resistance variations of +ΔR, +ΔR, −ΔR and −ΔR in correspondence to the magnetic field components f1y, f2y, f3y and f4y. Thus, when a voltage difference is applied between the contact V1 and the contact V3, there is a voltage difference, such as an output voltage Vy, existing between the contact V2 and the contact V4, and the output voltage Vy is, namely, a differential signal, in which a size thereof is corresponded to the size of the magnetic field component Hy. Therefore, by knowing the size of the output voltage Vy, it is able to deduce the size of the magnetic field component Hy.

Further, referring to FIG. 6C, when the external magnetic field has the magnetic field component Hz, the magnetoresistance units 200a, 200b, 200c and 200d respectively generate the resistance variations of +ΔR, −ΔR, +ΔR and −ΔR in correspondence to the magnetic field components f1z, f2z, f3z and f4z. Thus, when a voltage difference is applied between the contact V1 and the contact V3, a voltage difference between the contact V2 and the contact V4 is substantially 0, that is, a differential signal as currently being outputted is zero.

Accordingly, when the magnetoresistance units 200a, 200b, 200c and 200d are electrically connected to form the second kind of Wheatstone full bridge as shown in FIG. 6A to FIG. 6C, the magnetic field components Hx and Hz do not contribute to the voltage outputted by the contact V2 and V4. At this moment, the output voltage Vy is only related to the magnetic field component Hy, and thus the second kind of Wheatstone full bridge can be used to measure the magnetic field component Hy in the y-direction.

In the third period of the three different periods, referring to FIG. 7A again, the switching circuit 120 electrically connects the magnetoresistance units 200a, 200b, 200c and 200d to form the third kind of Wheatstone full bridge. In the third kind of Wheatstone full bridge: the magnetoresistance unit 200a and the magnetoresistance unit 200d are connected in series, the magnetoresistance unit 200b and the magnetoresistance unit 200c are connected in series, then the aforementioned two serial connections are further connected in parallel, the contact V2 is electrically connected between the magnetoresistance unit 200a and the magnetoresistance unit 200b, the contact V4 is electrically connected between the magnetoresistance unit 200c and the magnetoresistance unit 200d, the contact V1 is electrically connected between the magnetoresistance unit 200a and the magnetoresistance unit 200d, and the contact V3 is electrically connected between the magnetoresistance unit 200b and the magnetoresistance unit 200c. The setting directions of the initial magnetization directions of the magnetoresistance units 200a, 200b, 200c and 200d are identical to that of FIG. 5A to FIG. 5C, and thus when the external magnetic field has the magnetic field component Hx, the magnetoresistance units 200a, 200b, 200c and 200d also respectively generate the resistance variations of −ΔR, +ΔR, −ΔR and +ΔR in correspondence to the magnetic field components f1x, f2x, f3x and f4x. As a result, when a voltage difference is applied between the contact V2 and the contact V4, a voltage difference between the contact V1 and the contact V3 is substantially 0, that is, a differential signal as being outputted is 0.

On the other hand, referring to FIG. 7B, when the external magnetic field has the magnetic field component Hy, the magnetoresistance units 200a, 200b, 200c and 200d respectively generate the resistance variations of +ΔR, +ΔR, −ΔR and −ΔR in correspondence to the magnetic field components f1y, f1y, f3y and f4y. Thus, when a voltage difference is applied between the contact V2 and the contact V4, a voltage difference between the contact V1 and the contact V3 is substantially 0, namely, a differential signal as being outputted is 0.

Further, referring to FIG. 7C, when the external magnetic field has the magnetic field component Hz, the magnetoresistance units 200a, 200b, 200c and 200d respectively generate the resistance variations of +ΔR, −ΔR, +ΔR and −ΔR in correspondence to the magnetic field components f1z, f2z, f3z and f4z. Thus, when a voltage difference is applied between the contact V2 and the contact V4, there is a voltage difference, such as an output voltage Vz, existing between the contact V1 and the contact V3, and the output voltage Vz is, namely, a differential signal, in which a size thereof is corresponded to the size of the magnetic field component Hz. Therefore, by knowing the size of the output voltage Vz, it is able to deduce the size of the magnetic field component Hz.

Accordingly, when the magnetoresistance units 200a, 200b, 200c and 200d are electrically connected to form the third kind of Wheatstone full bridge as shown in FIG. 7A to FIG. 7C, the magnetic field components Hx and Hy do not contribute to the voltage outputted by the contact V1 and V3. At this moment, the output voltage Vz is only related to the magnetic field component Hz, and thus the third kind of Wheatstone full bridge can be used to measure the magnetic field component Hz in the z-direction.

As a result, after the first period, second period and the third period, the magnetic field sensing apparatus 100 can sequentially measure and obtain the magnetic field component Hx, the magnetic field component Hy and the magnetic field component Hz of the external magnetic field, so as to know the size and the direction of the external magnetic field. When the magnetic field sensing apparatus 100 continuously repeats to sequentially form the first, second and third kinds of Wheatstone full bridge in the first, second and third periods, the change of the external magnetic field with respect to the magnetic field sensing apparatus 100 can be continuously and timely monitored; that is, for an instance, a direction change of the magnetic field sensing apparatus 100 with respective to the geomagnetic field can be monitored.

Figure 8:
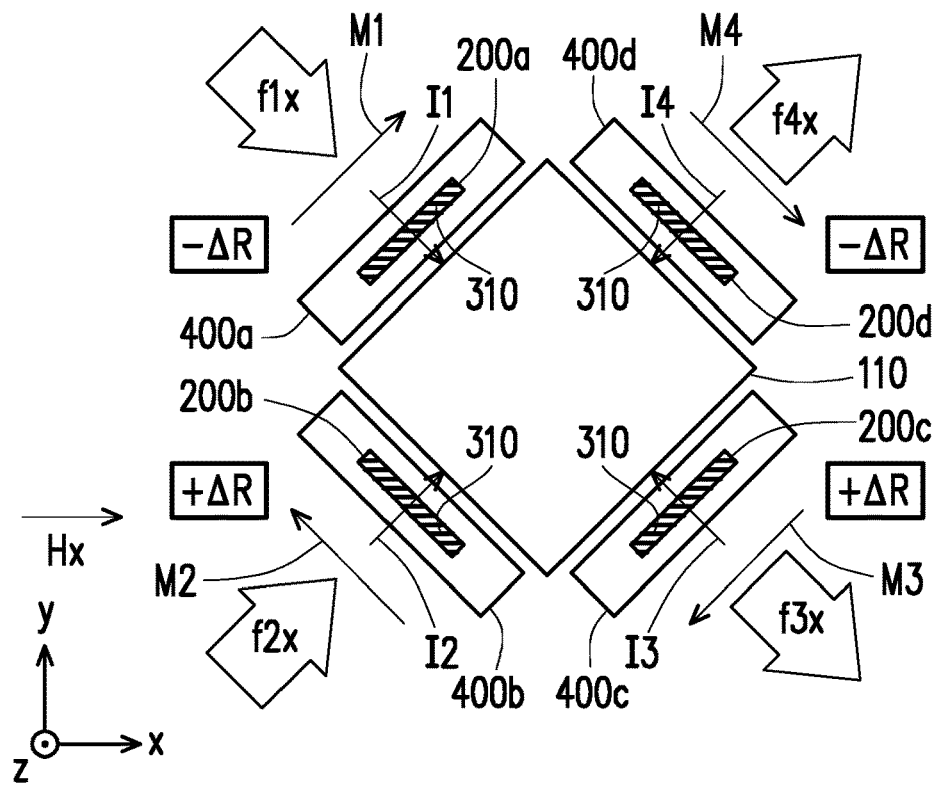
FIG. 8 illustrates a practical example of setting directions of electrical shorting bars and magnetization directions of the magnetoresistance units that are applicable to the three kinds of Wheatstone full bridges shown in FIG. 5A to FIG. 7C.

FIG. 8 illustrates a practical example of setting directions of electrical shorting bars and magnetization directions of the magnetoresistance units that are applicable to the three kinds of Wheatstone full bridges shown in FIG. 5A to FIG. 7C. Referring to FIG. 5A and FIG. 8, in the present embodiment, the electrical shorting bars 310 of the magnetoresistance units 200a, 200b, 200c and 200d are all extended towards the x-direction, the magnetization direction setting elements 400a, 400b, 400c and 400d are respectively disposed at the magnetoresistance units 200a, 200b, 200c and 200d, and conducted current directions of the magnetization direction setting elements 400a, 400b, 400c and 400d when respectively setting the magnetization directions of the magnetoresistance units 200a, 200b, 200c and 200d are respectively current directions I1, I2, I3 and I4, so that the initial magnetization directions of the magnetoresistance units 200a, 200b, 200c and 200d are respectively set as magnetization directions M1, M2, M3 and M4. The current direction I1 faces towards x−y direction, the current direction I2 faces towards x+y direction, the current direction I3 faces towards −x+y direction, the current direction I4 faces towards −x−y direction, the magnetization direction M1 faces towards x+y direction, the magnetization direction M2 faces towards −x+y direction, the magnetization direction M3 faces towards −x−y direction, and the magnetization direction M4 faces towards x−y direction. With the aforementioned configurations, when the external magnetic field has the magnetic field component Hx, the magnetoresistance units 200a, 200b, 200c and 200d are enabled to respectively generate the resistance variations of −ΔR, +ΔR, −ΔR and +ΔR (as the conditions shown in FIG. 5A, FIG. 6A and FIG. 7A), and are adapted to be applied to the conditions shown in FIG. 5B, FIG. 5C, FIG. 6B, FIG. 6C, FIG. 7B and FIG. 7C. However, the aforementioned magnetization directions M1~M4, the aforementioned current directions I1~I4 and the extending directions of the electrical shorting bars 310 of the aforementioned magnetoresistance units 200a, 200b, 200c and 200d are not limited to the practical example as shown in FIG. 8, and FIG. 8 merely provides one of a plurality different practical examples. For instance, the electrical shorting bars 310 of the magnetoresistance unit 200a in FIG. 8 can be changed to extend towards the y-direction, and the current direction I1 can also be reversed at the same time, such as being changed to face towards the −x+y direction, so that the magnetization direction M1 can be reversed, such as being changed to face towards the −x-y direction; and under this configuration, when there is a magnetic field component Hx as shown in FIG. 5A, the resistance variation of the magnetoresistance unit 200a is still maintained as −ΔR. Therefore, under this configuration, the measurement results of the magnetic field sensing apparatus 100 are still the same as the measurement results of FIG. 5A to FIG. 7C. In the similar rationales, other setting directions of the magnetoresistance units 200b, 200c and 200d can also be changed.

In addition, the combination of the resistance variations as shown in FIG. 5A to FIG. 7C is also merely one of the examples, such that the combination of the resistance variations may also undergo an equivalent change as long as the signal outputted by the three kinds of Wheatstone full bridges in any one of the three different periods is a differential signal corresponding to the magnetic field component of one of the three different directions, and the differential signals generated by the three kinds of Wheatstone full bridges and corresponding to the magnetic field components in the remaining two of the three different directions are both zero.

Moreover, an order of occurrence of the first period, the second period and the third period is also not limited, and it can be in any suitable arrangement. For instance, the order of occurrence may also sequentially be the second kind of Wheatstone full bridge, the first kind of Wheatstone full bridge and the third kind of Wheatstone full bridge, so as to sequentially measure the magnetic field component Hy, the magnetic field component Hx and the magnetic field component Hz.

In the magnetic field sensing apparatus 100 of the present embodiment, since one Wheatstone full bridge is being used in a period, the magnetic field components in the three different directions can be sensed at the three different periods, respectively, and thus the structure of the magnetic field sensing apparatus 100 is relatively simple and can have a smaller volume. As compared to a magnetic field sensing apparatus which uses three Wheatstone full bridges to respectively measure magnetic field components in three different directions, the volume of the magnetic field sensing apparatus 100 of the present embodiment can be reduced by a third, so that the volume magnetic field sensing apparatus 100 can be substantially reduced, and thereby lowers the manufacturing cost of the magnetic field sensing apparatus 100.

In addition, with the configuration in which the magnetization direction setting elements 400a~400d can initialize the magnetization directions of the magnetoresistance units 200a~200d, the magnetoresistance units 200a~200d, after being impacted by a strong external magnetic field, can still be used normally. Moreover, different configurations of the magnetization directions of the magnetoresistance units 200a~200d can be formed by changing the current directions of the magnetization direction setting elements 400a~400d, so as to measure dynamic system offsets of the magnetoresistance units 200a~200d. By subtracting the dynamic system offsets from the measured values, accurate values of the magnetic field components can be obtained more quickly. Similarly, low frequency noises can also be deducted to enable the measured values of the magnetic field components to become even more accurate.

Figure 9:
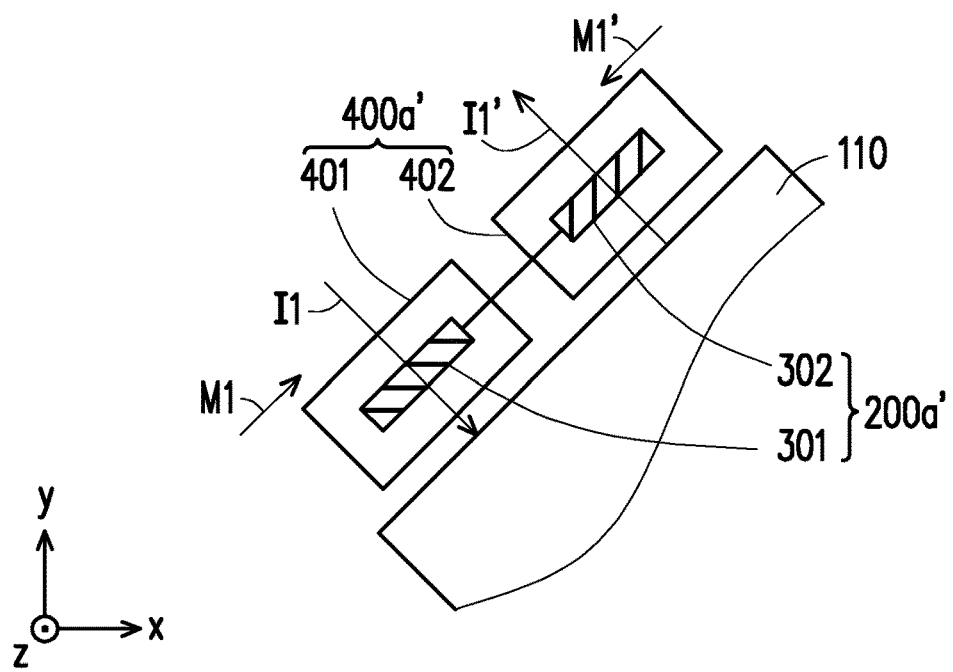
FIG. 9 is a schematic top view illustrating a magnetoresistance unit and a magnetization direction setting element according to another embodiment of the invention.

FIG. 9 is a schematic top view illustrating a magnetoresistance unit and a magnetization direction setting element according to another embodiment of the invention. Referring to FIG. 8 and FIG. 9, the magnetoresistance unit 200a in FIG. 8 is illustrated as having one anisotropic magnetoresistor 300 for an example, but the invention is not limited thereto. Each of the magnetoresistance units 200 can have a plurality of anisotropic magnetoresistors 300, such as a plurality of anisotropic magnetoresistors 300 connected in series, so as to increase an intensity of the output signal. For instance, in FIG. 9, a magnetoresistance unit 200a' has an anisotropic magnetoresistor 301 and an anisotropic magnetoresistor 302, wherein the relative configuration of the anisotropic magnetoresistor 301 can be the same as that of the magnetoresistance unit 200a in FIG. 8, and the relative configuration of the anisotropic magnetoresistor 302 can be the same as or different from the anisotropic magnetoresistor 301 (in FIG. 9, it is taken to be different for an example). In FIG. 9, the electrical shorting bars 310 of the anisotropic magnetoresistor 302 extend along the y-direction, and the magnetization direction setting elements 400a' can include two sub-magnetization direction setting elements 401 and 402 respectively disposed above the anisotropic magnetoresistors 301 and 302. By having a current direction I1' of the sub-magnetization direction setting element 402 to face towards the −x+y direction, an initial magnetization direction of the anisotropic magnetoresistor 302 is set as a magnetization direction M1'. As a result, when there is an external magnetic field having a magnetic field component Hx as shown in FIG. 5, the anisotropic magnetoresistor 301 and the anisotropic magnetoresistor 302 each generate a resistance variation of −ΔR, and the resistance variation becomes −2ΔR after the anisotropic magnetoresistor 301 and the anisotropic magnetoresistor 302 are being connected in series, and thus the output signal can be amplified.

Figure 10:
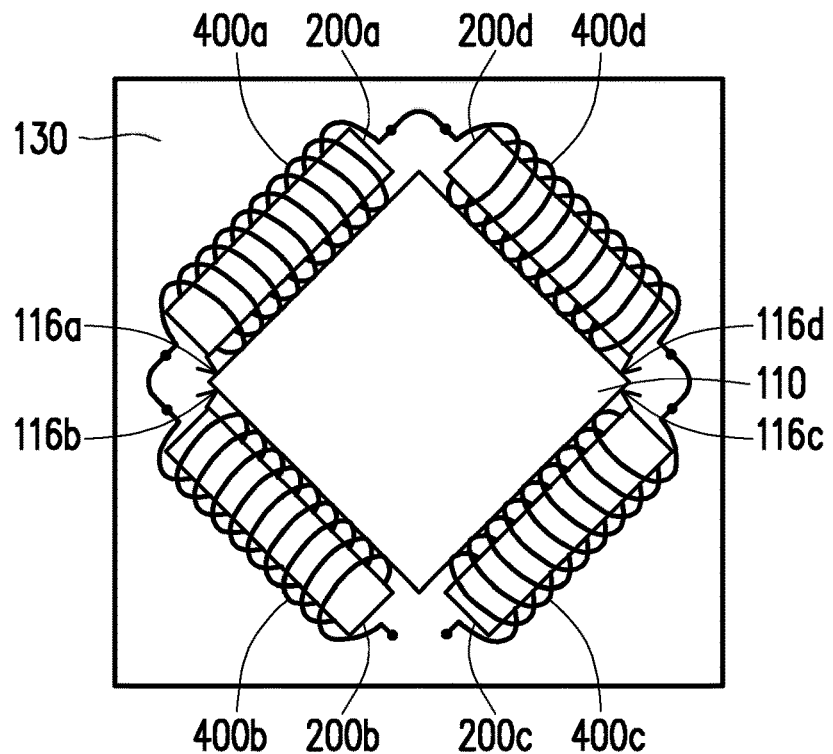
FIG. 10 illustrates a plurality of magnetization direction setting elements of FIG. 1A according to another embodiment.

FIG. 10 illustrates a plurality of magnetization direction setting elements of FIG. 1A according to another embodiment. Referring to FIG. 1A and FIG. 10, in the embodiment of FIG. 10, the magnetization direction setting elements 400b, 400a, 400d and 400c can be electrically connected by means of serial connection, so that the current can generate the magnetization directions M1, M2, M3 and M4 as shown in FIG. 8 at the magnetoresistance units 200a, 200b, 200c and 200d, respectively, when sequentially flowing through the magnetization direction setting elements 400b, 400a, 400d and 400c.

Figure 11:
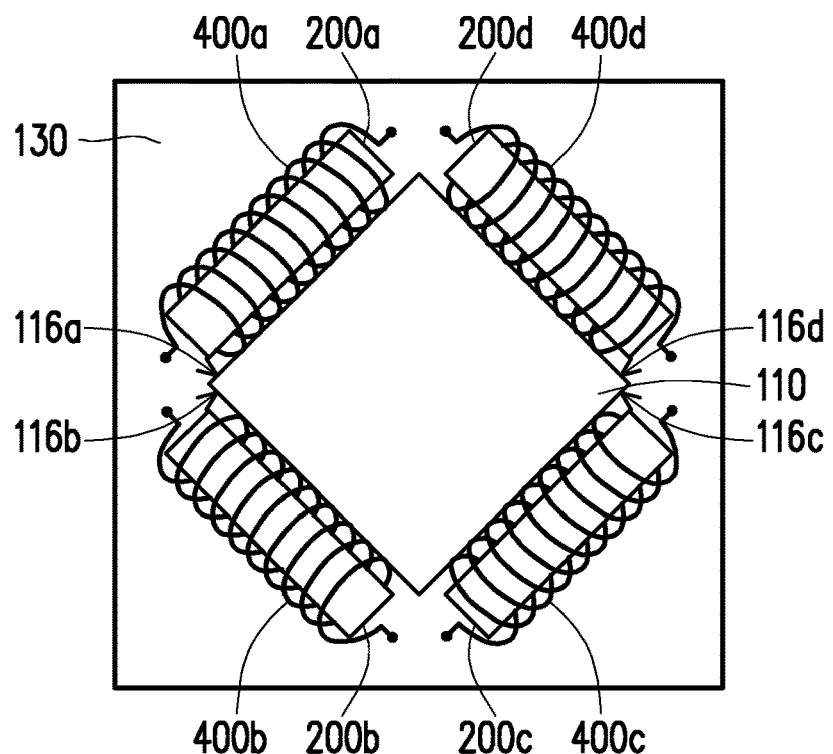
FIG. 11 illustrates a plurality of magnetization direction setting elements of FIG. 1A according to yet another embodiment.

FIG. 11 illustrates a plurality of magnetization direction setting elements of FIG. 1A according to yet another embodiment. Referring to FIG. 1A and FIG. 11, in the embodiment of FIG. 11, the magnetization direction setting elements 400a, 400b, 400c and 400d can be independently controlled, such as being controlled through the circuit in the substrate 130. As a result, the magnetoresistance units 200a, 200b, 200c and 200d can be connected with only one kind of Wheatstone full bridge, and the current directions of the magnetization direction setting elements 400a, 400b, 400c and 400d can be independently controlled to decide whether the different magnetic field components Hx, Hy and Hz are to generate a resistance variation of +ΔR or a resistance variation of −ΔR to the magnetoresistance units 200a, 200b, 200c and 200d at the first period to the third period, wherein the current directions may also be reversed so as to change the resistance variation from +ΔR to −ΔR or vice versa.

Figure 12A:
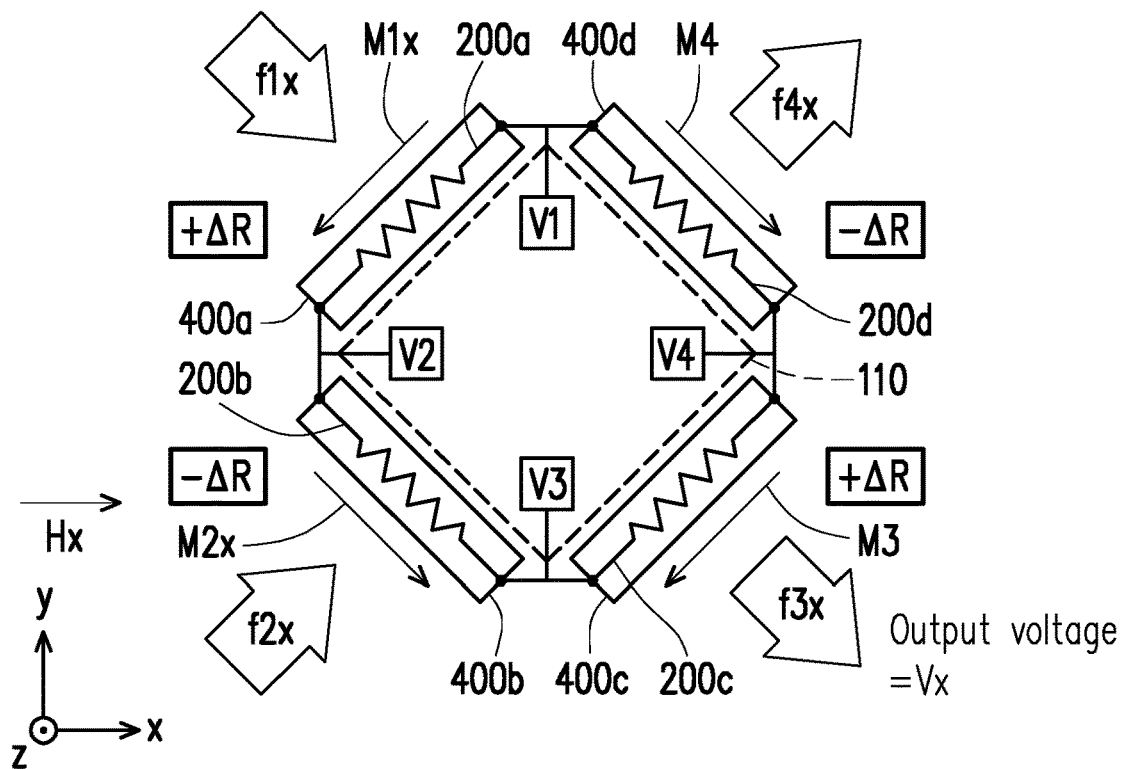
FIG. 12A, FIG. 12B and FIG. 12C are equivalent circuit diagrams of a magnetic field sensing apparatus in a second embodiment of the invention when measuring the magnetic field component in the x-direction.
Figure 12B:
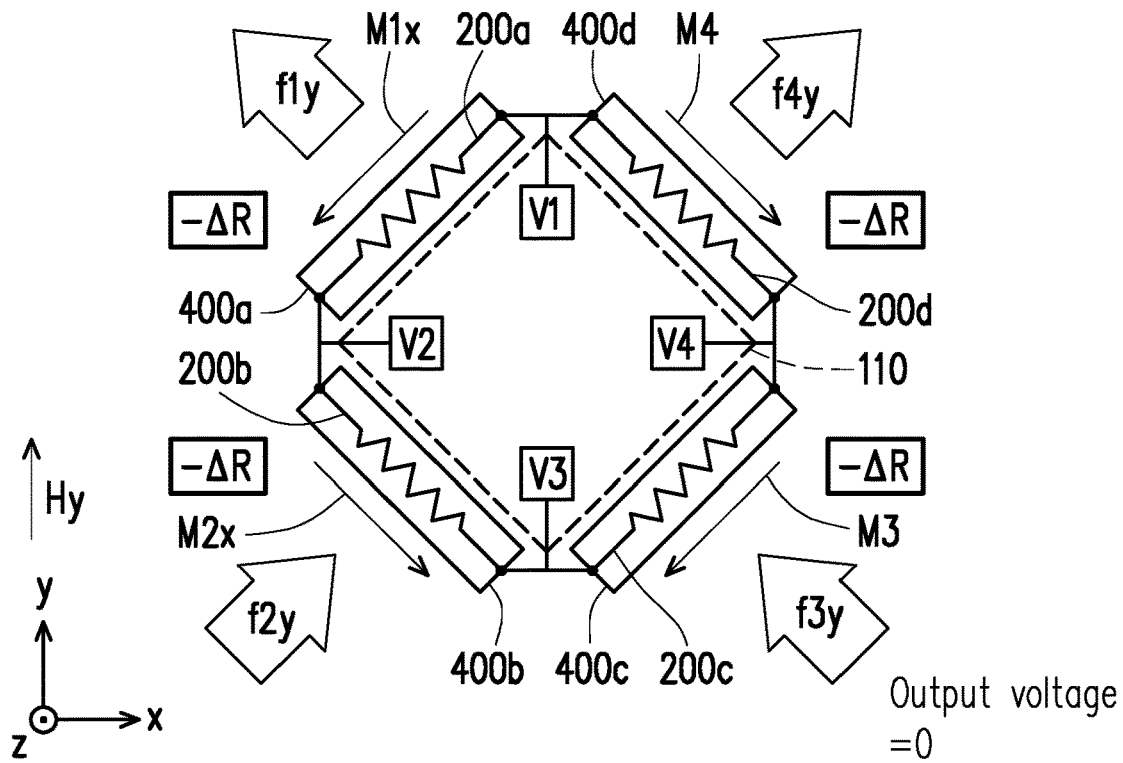
Figure 12C:
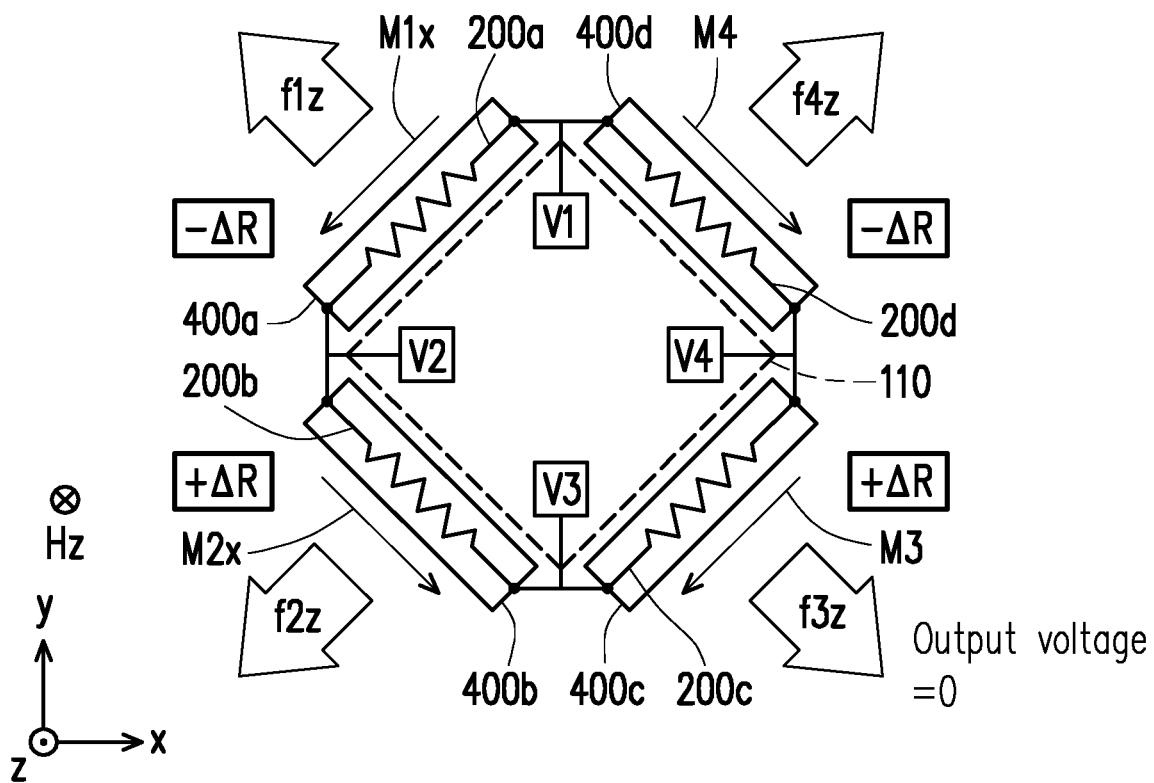
Figure 13A:
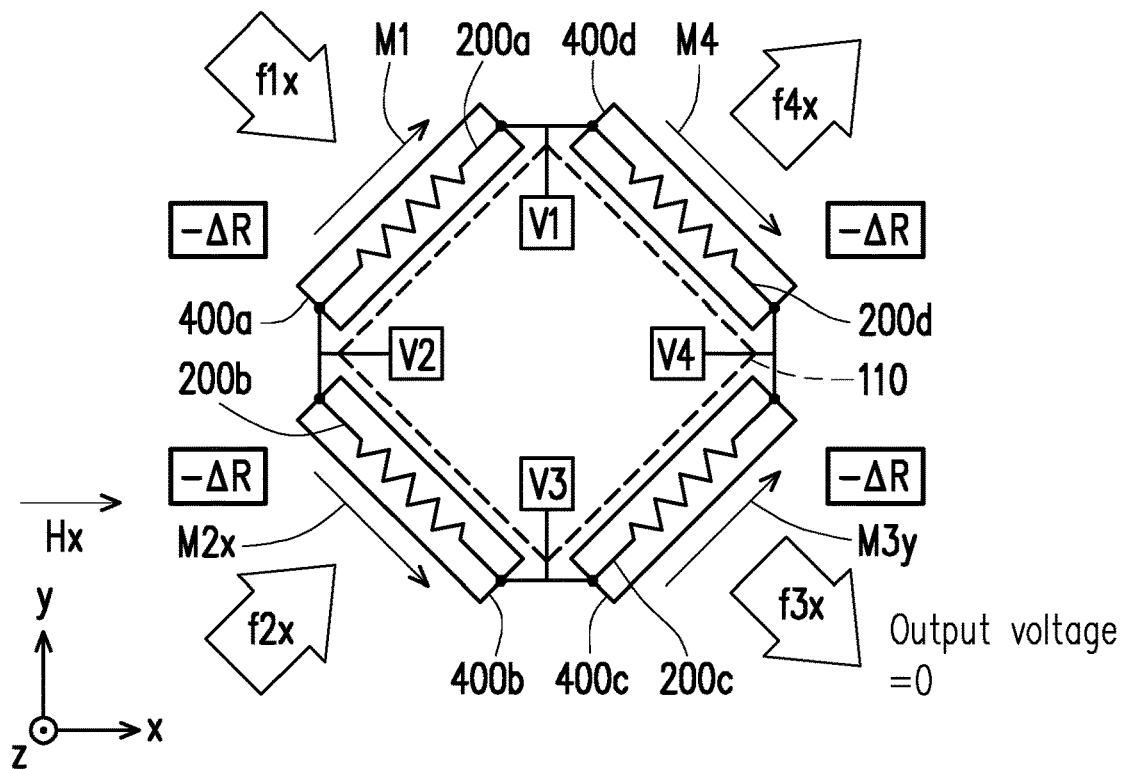
FIG. 13A, FIG. 13B and FIG. 13C are equivalent circuit diagrams of a magnetic field sensing apparatus in the second embodiment of the invention when measuring the magnetic field component in the y-direction.
Figure 13B:
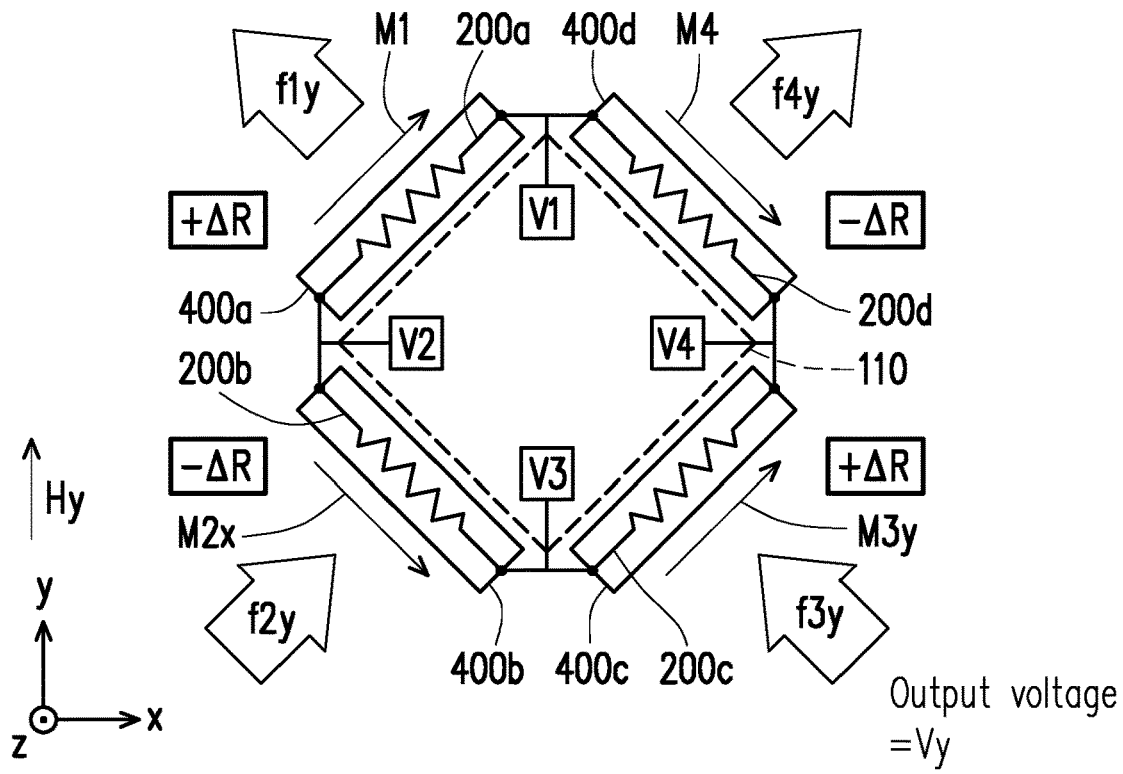
Figure 13C:
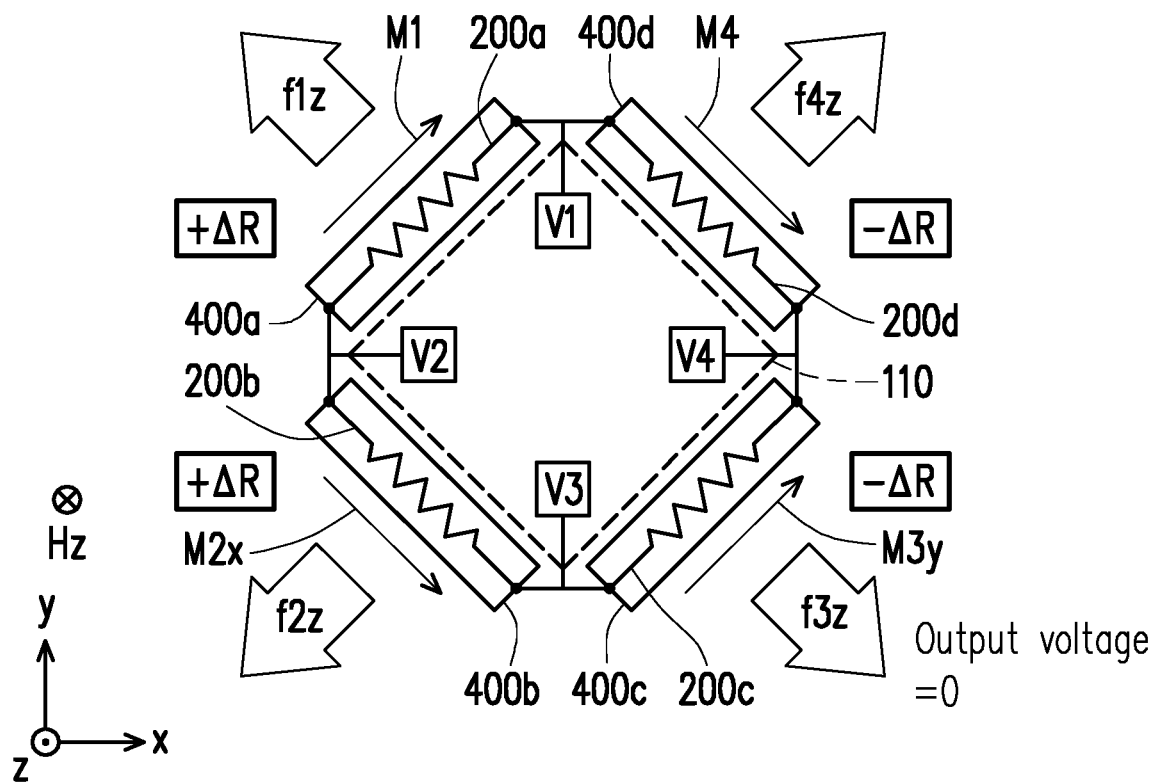
Figure 14A:
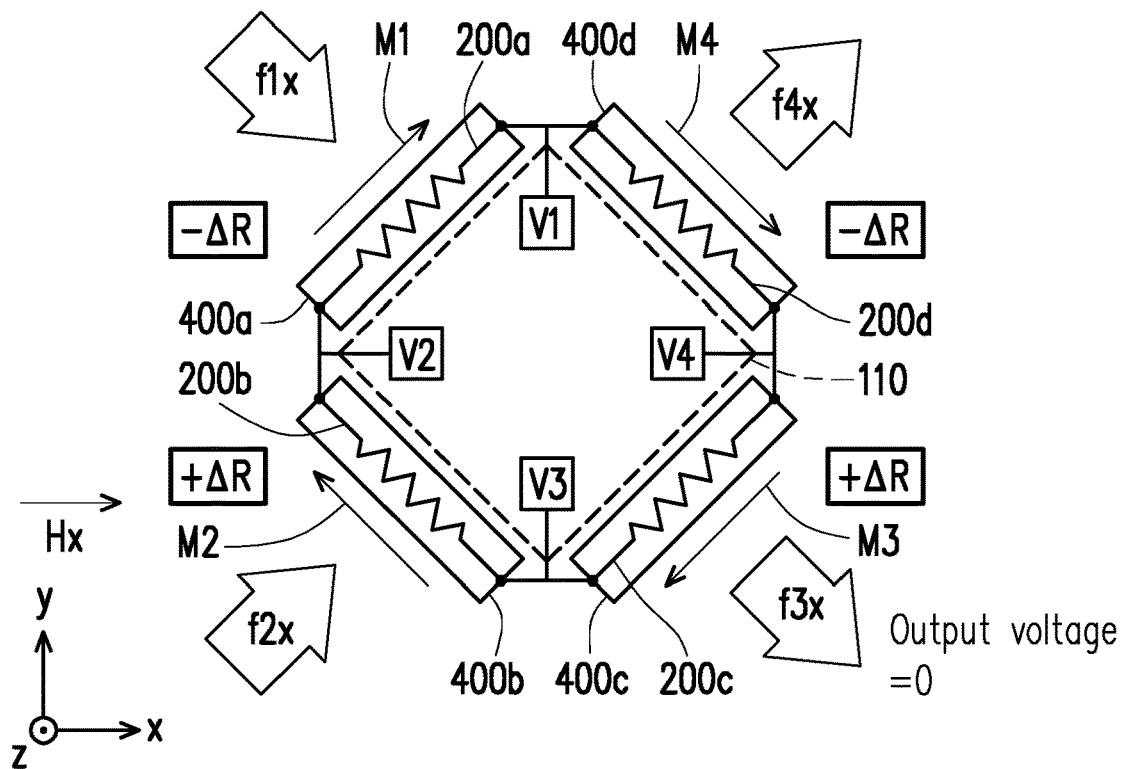
FIG. 14A, FIG. 14B and FIG. 14C are equivalent circuit diagrams of a magnetic field sensing apparatus in the second embodiment of the invention when measuring the magnetic field component in the z-direction.
Figure 14B:
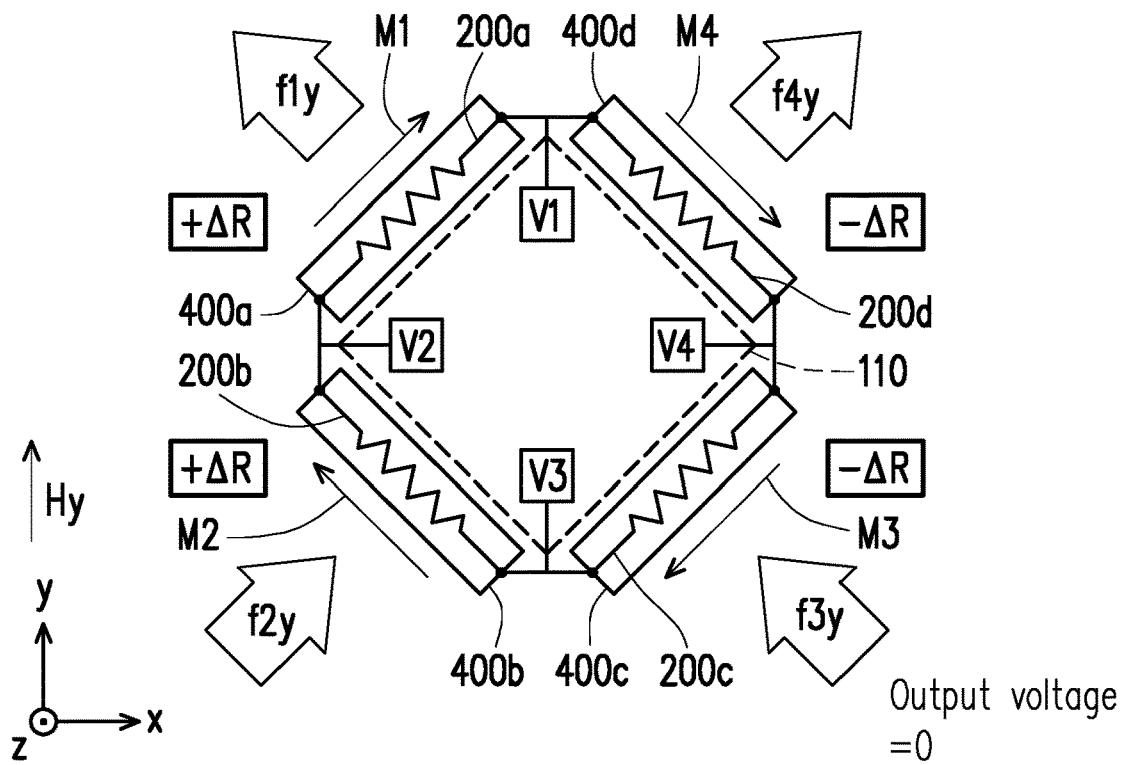
Figure 14C:
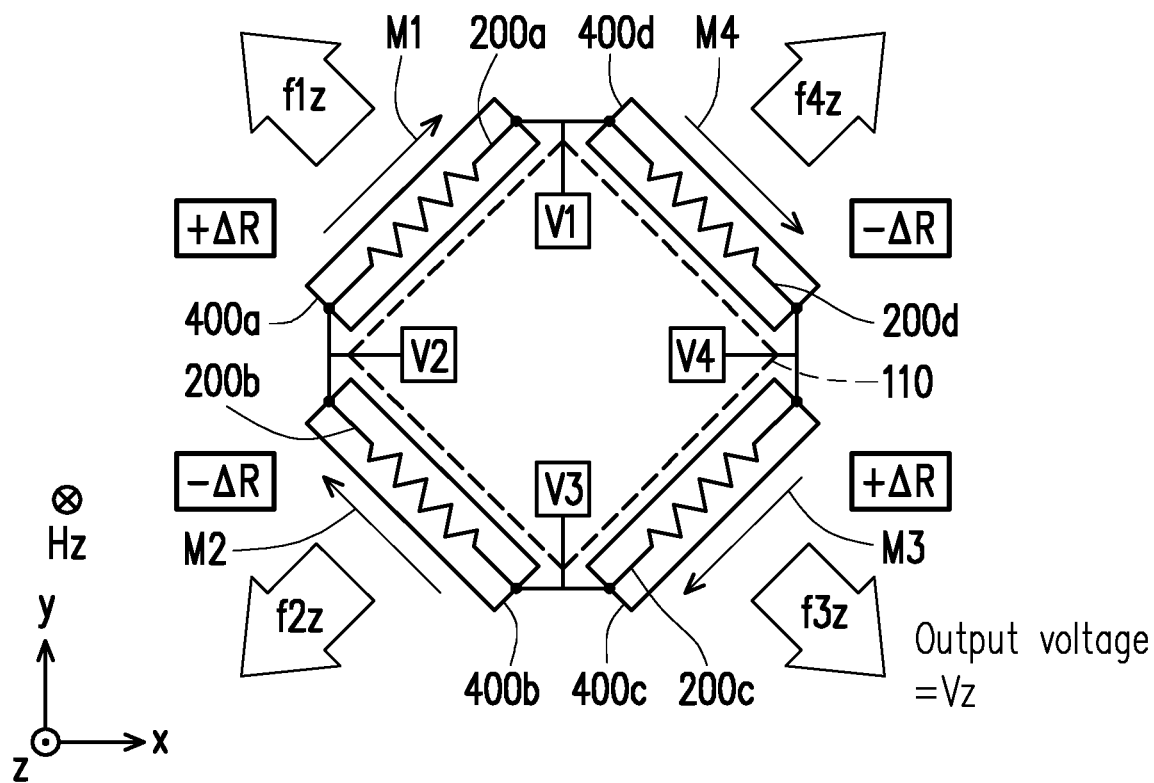

FIG. 12A, FIG. 12B and FIG. 12C are equivalent circuit diagrams of a magnetic field sensing apparatus in a second embodiment of the invention when measuring the magnetic field component in the x-direction, FIG. 13A, FIG. 13B and FIG. 13C are equivalent circuit diagrams of a magnetic field sensing apparatus in the second embodiment of the invention when measuring the magnetic field component in the y-direction, and FIG. 14A, FIG. 14B and FIG. 14C are equivalent circuit diagrams of a magnetic field sensing apparatus in the second embodiment of the invention when measuring the magnetic field component in the z-direction. The magnetic field sensing apparatus 100 of the second embodiment adopts the independently controlled framework of the magnetization direction setting elements 400a, 400b, 400c and 400d of FIG. 11, and the magnetoresistance units 200a, 200b, 200c and 200d are connected to form only one kind of Wheatstone full bridge which is unchangeable.

In the present embodiment, the magnetization direction setting elements 400a, 400b, 400c and 400d respectively set the magnetization directions of the magnetoresistance units 200a, 200b, 200c and 200d into three different combinations in three different periods, so as to enable the one kind of Wheatstone full bridge to respectively measure the magnetic field components Hx, Hy and Hz in three different directions in the three different periods and to respectively output three signals corresponding to the magnetic field components Hx, Hy and Hz in the three different directions.

Specifically, in the first period of the three different periods, referring firstly to FIG. 12A, when the external magnetic field has the magnetic field component Hx, by using the magnetization direction setting elements 400a, 400b, 400c and 400d to independently set the initial magnetization directions of the magnetoresistance units 200a, 200b, 200c and 200d respectively to an appropriate direction combination (hereinafter "the first kind of combination"), the magnetoresistance units 200a, 200b, 200c and 200d can respectively generate the resistance variations of +ΔR, −ΔR, +ΔR and −ΔR in correspondence to the magnetic field components f1x, f2x, f3x and f4x. For instance, when the electrical shorting bars of the magnetoresistance units 200a, 200b, 200c and 200d in FIG. 12A to FIG. 14C are all extending towards the x-direction as shown in FIG. 8, the first kind of combination indicates that the magnetization direction setting elements 400a, 400b, 400c and 400d set the magnetoresistance units 200a, 200b, 200c and 200d with the magnetization directions M1x, M2x, M3 and M4, respectively, wherein the magnetization direction M1x is reverse to the magnetization direction M1 of FIG. 8, and the magnetization direction M2x is reverse to the magnetization direction M2 of FIG. 8. That is to say, the current direction of the magnetization direction setting elements 400a in FIG. 12A to FIG. 12C is opposite to the current direction of the magnetization direction setting element 400a in FIG. 8, and the current direction of the magnetization direction setting element 400b in FIG. 12A to FIG. 12C is opposite to the current direction of the magnetization direction setting element 400b in FIG. 8.

In addition, different from the first embodiment, the second embodiment includes only one kind of Wheatstone full bridge which is unchangeable. For instance, in this kind of Wheatstone full bridge: the magnetoresistance unit 200a and the magnetoresistance unit 200d are connected in series, the magnetoresistance unit 200b and the magnetoresistance unit 200c are connected in series, then the aforementioned two serial connections are further connected in parallel, the contact V2 is electrically connected between the magnetoresistance unit 200a and the magnetoresistance unit 200b, the contact V4 is electrically connected between the magnetoresistance unit 200c and the magnetoresistance unit 200d, the contact V1 is electrically connected between the magnetoresistance unit 200a and the magnetoresistance unit 200d, and the contact V3 is electrically connected between the magnetoresistance unit 200b and the magnetoresistance unit 200c. However, in other embodiments, this kind of unchangeable Wheatstone full bridge may also be the kind of Wheatstone full bridge as shown in FIG. 5A to FIG. 5C, the kind of Wheatstone full bridge as shown in FIG. 6A to FIG. 6C or other suitable type of Wheatstone full bridge.

Under the framework of the kind of Wheatstone full bridge as shown in FIG. 12A, the magnetoresistance units 200a, 200b, 200c and 200d respectively generate the resistance variations of +ΔR, −ΔR, +ΔR and −ΔR as described in the above, and when a voltage difference is applied between the contact V2 and the contact V4, there is a voltage difference, such as an output voltage Vx, existing between the contact V1 and the contact V3, and the output voltage Vx is, namely, a differential signal, in which a size thereof is corresponded to the size of the magnetic field component Hx. Therefore, by knowing the size of the output voltage Vx, it is able to deduce the size of the magnetic field component Hx.

Referring further to FIG. 12B, when the external magnetic field has the magnetic field component Hy, the magnetoresistance units 200a, 200b, 200c and 200d respectively generate the resistance variations of −ΔR, −ΔR, −ΔR and −ΔR in correspondence to the magnetic field components f1y, f1y, f3y and f4y. Therefore, when a voltage difference is applied between the contact V2 and the contact V4, a voltage difference between the contact V1 and the contact V3 is substantially 0, that is, the differential signal as currently outputted is zero.

Referring to FIG. 12C, when the external magnetic field has the magnetic field component Hz, the magnetoresistance units 200a, 200b, 200c and 200d respectively generate the resistance variations of −ΔR, +ΔR, +ΔR and −ΔR in correspondence to the magnetic field components f1z, f2z, f3z and f4z. Therefore, when a voltage difference is applied between the contact V2 and the contact V4, a voltage difference between the contact V1 and the contact V3 is substantially 0, that is, the differential signal as currently outputted is zero.

Accordingly, under the setting combination (i.e., the aforementioned first kind of combination) of the initial magnetization directions of the magnetoresistance units 200a, 200b, 200c and 200d in FIG. 12A to FIG. 12C, the magnetic field components Hy and Hz do not contribute to the voltage outputted by the contact V1 and V3. At this moment, the output voltage Vx is only related to the magnetic field component Hx, and thus this kind of setting combination of the magnetization direction can be used to measure the magnetic field component Hx in the x-direction.

In the second period of the three different period, referring firstly to FIG. 13A, when the external magnetic field has the magnetic field component Hx, by using the magnetization direction setting elements 400a, 400b, 400c and 400d to independently set the initial magnetization directions of the magnetoresistance units 200a, 200b, 200c and 200d respectively to another appropriate direction combination (hereinafter "second kind of combination"), the magnetoresistance units 200a, 200b, 200c and 200d can respectively generate the resistance variations of −ΔR, −ΔR, −ΔR and −ΔR in correspondence to the magnetic field components f1x, f2x, f3x and f4x. As compared to FIG. 12A, the current direction of the magnetization direction setting element 400a in FIG. 13A is opposite to the current direction of the magnetization direction setting element 400a in FIG. 12A, and thus the initial magnetization direction M1 of the magnetoresistance unit 200a in FIG. 13A is opposite to the initial magnetization direction M1x of the magnetoresistance unit 200a in FIG. 12A, so that the magnetoresistance unit 200a in FIG. 12A has a resistance variation of +ΔR, but the magnetoresistance unit 200a in FIG. 13A generates a resistance variation of −ΔR. Similarly, as compared to the FIG. 12A, the current direction of the magnetization direction setting element 400c in FIG. 13A is opposite to the current direction of the magnetization direction setting element 400c in FIG. 12A, and thus the initial magnetization direction M3y of the magnetoresistance unit 200c in FIG. 13A is opposite to the initial magnetization direction M3 of the magnetoresistance unit 200c in FIG. 12A, so that the magnetoresistance unit 200c in FIG. 12A has a resistance variation of +ΔR, but the magnetoresistance unit 200c in FIG. 13A generates a resistance variation of −ΔR. Moreover, the current direction of the magnetization direction setting element 400b in FIG. 13A maintains the same as the current direction of the magnetization direction setting element 400b in FIG. 12A, and the current direction of the magnetization direction setting element 400d in FIG. 13A maintains the same as the current direction of the magnetization direction setting element 400d in FIG. 12A.

In addition, the Wheatstone full bridge in FIG. 13A is the same as the Wheatstone full bridge in FIG. 12A and has no change. Under the framework of the kind of Wheatstone frill bridge in FIG. 13A, the magnetoresistance units 200a, 200b, 200c and 200d respectively generate the resistance variations of −ΔR, −ΔR, −ΔR and −ΔR as described in the above, and when a voltage difference is applied between the contact V2 and the contact V4, a voltage difference between the contact V1 and the contact V3 is substantially 0, that is, the differential signal as currently outputted is zero.

Referring to FIG. 13B, when the external magnetic field has the magnetic field component Hy, the magnetoresistance units 200a, 200b, 200c and 200d respectively generate the resistance variations of +ΔR, −ΔR, +ΔR and −ΔR in correspondence to the magnetic field components f1y, f2y, f3y and f4y. Therefore, when a voltage difference is applied between the contact V2 and the contact V4, there is a voltage difference, such as an output voltage Vy, existing between the contact V1 and the contact V3, and the output voltage Vy is, namely, a differential signal, in which a size thereof is corresponded to the size of the magnetic field component Hy. Therefore, by knowing the size of the output voltage Vy, it is able to deduce the size of the magnetic field component Hy.

Referring to FIG. 13C, when the external magnetic field has the magnetic field component Hz, the magnetoresistance units 200a, 200b, 200c and 200d respectively generate the resistance variations of +ΔR, +ΔR, −ΔR and −ΔR in correspondence to the magnetic field components f1z, f2z, f3z and f4z. Therefore, when a voltage difference is applied between the contact V2 and the contact V4, a voltage difference between the contact V1 and the contact V3 is substantially 0, that is, the differential signal as currently outputted is zero.

Accordingly, under the setting combination (i.e., the aforementioned second kind of combination) of the initial magnetization directions of the magnetoresistance units 200a, 200b, 200c and 200d in FIG. 13A to FIG. 13C, the magnetic field components Hx and Hz do not contribute to the voltage outputted by the contact V1 and V3. At this moment, the output voltage Vy is only related to the magnetic field component Hy, and thus this kind of setting combination of the magnetization direction can be used to measure the magnetic field component Hy in the y-direction.

In the third period of the three different periods, referring firstly to FIG. 14A, when the external magnetic field has the magnetic field component Hx, by using the magnetization direction setting elements 400a, 400b, 400c and 400d to independently set the initial magnetization directions of the magnetoresistance units 200a, 200b, 200c and 200d respectively to yet another appropriate direction combination (hereinafter "third kind of combination"; namely, the combination of magnetization directions M1, M2, M3 and M4), the magnetoresistance units 200a, 200b, 200c and 200d can respectively generate the resistance variations of −ΔR, +ΔR, +ΔR and −ΔR in correspondence to the magnetic field components f1x, f2x, f3x and f4x. As compared to FIG. 12A, the current direction of the magnetization direction setting element 400a in FIG. 14A is opposite to the current direction of the magnetization direction setting element 400a in FIG. 12A, and thus the initial magnetization direction M1 of the magnetoresistance unit 200a in FIG. 14A is opposite to the initial magnetization direction M1x of the magnetoresistance unit 200a in FIG. 12A, so that the magnetoresistance unit 200a in FIG. 12A has a resistance variation of +ΔR, but the magnetoresistance unit 200a in FIG. 14A generates a resistance variation of −ΔR. Similarly, as compared to FIG. 12A, the current direction of the magnetization direction setting element 400b in FIG. 14A is opposite to the current direction of the magnetization direction setting element 400b in FIG. 12A, and thus the initial magnetization direction M2 of the magnetoresistance unit 200b in FIG. 14A is opposite to the initial magnetization direction M2x of the magnetoresistance unit 200b in FIG. 12A, so that the magnetoresistance unit 200b in FIG. 12A has a resistance variation of −ΔR, but the magnetoresistance unit 200b in FIG. 14A generates a resistance variation of +ΔR. Moreover, the current direction of the magnetization direction setting element 400c in FIG. 14A maintains the same as the current direction of the magnetization direction setting element 400c in FIG. 12A, and the current direction of the magnetization direction setting element 400d in FIG. 14A maintains the same as the current direction of the magnetization direction setting element 400d in FIG. 12A.

In addition, the Wheatstone full bridge in FIG. 14A is the same as the Wheatstone full bridge in FIG. 12A and has no change. Under the framework of the kind of Wheatstone full bridge in FIG. 14A, the magnetoresistance units 200a, 200b, 200c and 200d respectively generate the resistance variations of −ΔR, +ΔR, +ΔR and −ΔR as described in the above, and when a voltage difference is applied between the contact V2 and the contact V4, a voltage difference between the contact V1 and the contact V3 is substantially 0, that is, the differential signal as currently outputted is zero.

Referring to FIG. 14B, when the external magnetic field has the magnetic field component Hy, the magnetoresistance units 200a, 200b, 200c and 200d respectively generate the resistance variations of +ΔR, +ΔR, −ΔR and −ΔR in correspondence to the magnetic field components f1y, f2y, f3y and f4y. Therefore, when a voltage difference is applied between the contact V2 and the contact V4, a voltage difference between the contact V1 and the contact V3 is substantially 0, that is, the differential signal as currently outputted is zero.

Referring to FIG. 14C, when the external magnetic field has the magnetic field component Hz, the magnetoresistance units 200a, 200b, 200c and 200d respectively generate the resistance variations of +ΔR, −ΔR, +ΔR and −ΔR in correspondence to the magnetic field components f1z, f2z, f3z and f4z. Therefore, when a voltage difference is applied between the contact V2 and the contact V4, there is a voltage difference, such as an output voltage Vz, existing between the contact V1 and the contact V3, in which a size thereof is corresponded to the size of the magnetic field component Hz. Therefore, by knowing the size of the output voltage Vz, it is able to deduce the size of the magnetic field component Hz.

Accordingly, under the setting combination (i.e., the aforementioned third kind of combination) of the initial magnetization directions of the magnetoresistance units 200a, 200b, 200c and 200d in FIG. 14A to FIG. 14C, the magnetic field components Hx and Hy do not contribute to the voltage outputted by the contact V1 and V3. At this moment, the output voltage Vz is only related to the magnetic field component Hz, and thus this kind of setting combination of the magnetization direction can be used to measure the magnetic field component Hz in the z-direction.

As a result, after the first period, the second period and the third period, the magnetic field sensing apparatus 100 can sequentially measure and obtain the magnetic field component Hx, the magnetic field component Hy and the magnetic field component Hz of the external magnetic field, so as to know the size and the direction of the external magnetic field. When the magnetic field sensing apparatus 100 continuously repeats to sequentially form the first, second and third kinds of combination of the setting directions of the magnetization directions in the first, second and third periods, the change of the external magnetic field with respect to the magnetic field sensing apparatus 100 can be continuously and timely monitored, such that, for an instance, a direction change of the magnetic field sensing apparatus 100 with respective to the geomagnetic field can be monitored. Moreover, an order of occurrence of the first period, the second period and the third period is also not limited, such that it can be in any suitable arrangement.

In summary, in the magnetic field sensing apparatus of the embodiments of the invention, the magnetic flux concentrator is used to cause the magnetic field components in the three different directions to bend to the directions that can be sensed by the magnetoresistance units, and the magnetic field components in the three different directions, after being bent, have three different combinations with of directions passing through the magnetoresistance units. As a result, by electrically connecting the magnetoresistance units to form the at least one kind of Wheatstone full bridge in the three different periods, the magnetic field components in the three different directions can be respectively measured, and the at least one kind of Wheatstone full bridge can respectively output the three signals corresponding to the magnetic field components in the three different directions. Accordingly, the magnetic field sensing apparatus in the embodiments of the invention can have a simplified structure while simultaneously achieving a triaxial magnetic field measurement, and thus can further have a smaller volume.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A magnetic field sensing apparatus, comprising:
    a magnetic flux concentrator, having a top surface, a bottom surface opposite to the top surface, and a plurality of side surfaces connecting the top surface and the bottom surface;
    a plurality of magnetoresistance units, respectively disposed beside the side surfaces, wherein the magnetoresistance units are electrically connected to form an unchangeable Wheatstone full bridge; and
    a plurality of magnetization direction setting elements respectively disposed beside the magnetoresistance units so as to set magnetization directions of the magnetoresistance units, respectively, wherein the magnetization direction setting elements set the magnetization directions of the magnetoresistance units into three different combinations in three different periods, respectively, so as to enable the unchangeable Wheatstone full bridge to respectively measure the magnetic field components in the three different directions in the three different periods and to respectively output three signals corresponding to the magnetic field components in the three different directions.

2. The magnetic field sensing apparatus as recited in claim 1, wherein in any one of the three different periods, the signal outputted by the unchangeable Wheatstone full bridge is a differential signal corresponding to a magnetic field component in one of the three different directions, and at this moment, differential signals generated by the unchangeable Wheatstone full bridge and corresponding to magnetic field components in the remaining two of the three different directions are both zero.

3. The magnetic field sensing apparatus as recited in claim 1, wherein each of the magnetoresistance units comprises at least one anisotropic magnetoresistor.

4. The magnetic field sensing apparatus as recited in claim 3, wherein an extending direction of the anisotropic magnetoresistor in each of the magnetoresistance units is substantially parallel to the corresponding side surface, and is substantially parallel to the top surface and the bottom surface.

5. The magnetic field sensing apparatus as recited in claim 1, wherein the side surfaces are four side surfaces, normal lines of two adjacent side surfaces are substantially perpendicular to each other, the three different directions are a first direction, a second direction and a third direction, the first direction and the second direction fall on a plane parallel to a plurality of normal lines of the four side surfaces and substantially form an included angle of 45 degrees with the normal lines, the first direction and the second direction are substantially perpendicular to each other, and the third direction is substantially perpendicular to the first direction and the second direction.

6. The magnetic field sensing apparatus as recited in claim 1, wherein a material of the magnetic flux concentrator comprises a ferromagnetic material with a magnetic permeability greater than 10.

7. The magnetic field sensing apparatus as recited in claim 1, wherein a residual magnetism of the magnetic flux concentrator is less than 10% of a saturated magnetization thereof.

8. The magnetic field sensing apparatus as recited in claim 1, wherein two diagonal lines of the bottom surface are substantially parallel to two of the three different directions, respectively, and the remaining one of the three different directions is substantially perpendicular to the bottom surface.

9. The magnetic field sensing apparatus as recited in claim 1, further comprising a substrate, wherein the magnetic flux concentrator and the magnetoresistance units are disposed on the substrate, and the substrate is a semiconductor substrate, a glass substrate or a circuit substrate.

10. A magnetic field sensing apparatus, comprising:
    a magnetic flux concentrator, having a top surface, a bottom surface opposite to the top surface, and four side surfaces connecting the top surface and the bottom surface;
    at least four magnetoresistance units, respectively disposed beside the four side surfaces, wherein the at least four magnetoresistance units are electrically connected to form an unchangeable Wheatstone full bridge; and
    a plurality of magnetization direction setting elements respectively disposed beside the at least four magnetoresistance units so as to set magnetization directions of the at least four magnetoresistance units, respectively, wherein the magnetization direction setting elements set the magnetization directions of the at least four magnetoresistance units in a configuration that enables the unchangeable Wheatstone full bridge to measure a magnetic field components in a direction perpendicular to the top surface and to output a signal corresponding to the magnetic field component in the direction perpendicular to the top surface.

11. The magnetic field sensing apparatus as recited in claim 10, wherein the signal outputted by the unchangeable Wheatstone full bridge is a differential signal corresponding to the magnetic field component in the direction perpendicular to the top surface, and differential signals generated by the unchangeable Wheatstone full bridge and corresponding to magnetic field components in directions parallel to the top surface are zero.

12. The magnetic field sensing apparatus as recited in claim 10, wherein each of the at least four magnetoresistance units comprises at least one anisotropic magnetoresistor.

13. The magnetic field sensing apparatus as recited in claim 12, wherein an extending direction of the anisotropic magnetoresistor in each of the at least four magnetoresistance units is substantially parallel to the corresponding side surface, and is substantially parallel to the top surface and the bottom surface.

14. The magnetic field sensing apparatus as recited in claim 10, wherein normal lines of two adjacent side surfaces are substantially perpendicular to each other.

15. The magnetic field sensing apparatus as recited in claim 10, wherein a material of the magnetic flux concentrator comprises a ferromagnetic material with a magnetic permeability greater than 10.

16. The magnetic field sensing apparatus as recited in claim 10, wherein a residual magnetism of the magnetic flux concentrator is less than 10% of a saturated magnetization thereof.

17. The magnetic field sensing apparatus as recited in claim 10, wherein two diagonal lines of the bottom surface are substantially perpendicular to the top surface, and the direction perpendicular to the top surface is also perpendicular to the bottom surface.

18. The magnetic field sensing apparatus as recited in claim 10, further comprising a substrate, wherein the magnetic flux concentrator and the at least four magnetoresistance units are disposed on the substrate, and the substrate is a semiconductor substrate, a glass substrate or a circuit substrate.

19. A magnetic field sensing apparatus, comprising:
a magnetic flux concentrator, having a top surface, a bottom surface opposite to the top surface, and a plurality of side surfaces connecting the top surface and the bottom surface;
a plurality of magnetoresistance units, respectively disposed beside the side surfaces, wherein the magnetoresistance units are electrically connected to form an unchangeable Wheatstone full bridge; and
a plurality of magnetization direction setting elements respectively disposed beside the magnetoresistance units so as to set magnetization directions of the magnetoresistance units, respectively, wherein the magnetization direction setting elements set the magnetization directions of the magnetoresistance units into two different combinations in two different periods, respectively, so as to enable the unchangeable Wheatstone full bridge to respectively measure the magnetic field components in the two different directions in the two different periods and to respectively output two signals corresponding to the magnetic field components in the two different directions.

20. A magnetic field sensing apparatus, comprising:
a magnetic flux concentrator, having a top surface, a bottom surface opposite to the top surface, and four side surfaces connecting the top surface and the bottom surface;
at least four magnetoresistance units, respectively disposed beside the four side surfaces, wherein the at least four magnetoresistance units are electrically connected into two different combinations to form two kinds of Wheatstone full bridges in two different periods, respectively, so as to measure magnetic field components in two different directions and to cause the two kinds of the Wheatstone full bridges to respectively output two signals corresponding to the magnetic field components in the two different directions, wherein in any one of the two different periods, the number of the Wheatstone full bridge formed by electrically connecting the at least four magnetoresistance units is one; and
a switching circuit, electrically connected to the at least four magnetoresistance units, wherein the switching circuit electrically connects the at least four magnetoresistance units into the two different combinations to form the two kinds of Wheatstone full bridges, respectively, and the two kinds of Wheatstone full bridges respectively measure the magnetic field components at the two different directions and respectively output the two signals corresponding to the magnetic field components in the two different directions.

* * * * *